United States Patent
Kitamura et al.

(10) Patent No.: US 11,173,638 B2
(45) Date of Patent: Nov. 16, 2021

(54) MOLDED PRODUCT PRODUCTION SYSTEM

(71) Applicant: KIKUSUI SEISAKUSHO LTD., Kyoto (JP)

(72) Inventors: Naoshige Kitamura, Kyoto (JP); Jun Oyama, Kyoto (JP); Masaoki Murakoshi, Tokyo (JP)

(73) Assignee: KIKUSUI SEISAKUSHO LTD., Kyoto (JP)

( * ) Notice: Subject to any disclaimer, the term of this patent is extended or adjusted under 35 U.S.C. 154(b) by 486 days.

(21) Appl. No.: 15/422,292

(22) Filed: Feb. 1, 2017

(65) Prior Publication Data

US 2017/0282420 A1    Oct. 5, 2017

(30) Foreign Application Priority Data

Mar. 29, 2016 (JP) .............................. JP2016-065886

(51) Int. Cl.
*B29C 43/58* (2006.01)
*B30B 15/26* (2006.01)
(Continued)

(52) U.S. Cl.
CPC ............ *B29C 43/58* (2013.01); *A61K 9/2095* (2013.01); *B01F 3/188* (2013.01);
(Continued)

(58) Field of Classification Search
CPC ......... B29C 43/58; B29C 43/02; B29C 43/34; B30B 11/08; B30B 11/005
See application file for complete search history.

(56) References Cited

U.S. PATENT DOCUMENTS

| 2,242,189 A | 5/1941 | Zelov |
| 2,803,852 A | 8/1957 | Cook |

(Continued)

FOREIGN PATENT DOCUMENTS

| CN | 103313924 A | 9/2013 |
| JP | 2002-522198 A | 7/2002 |

(Continued)

OTHER PUBLICATIONS

United States Office Action dated May 22, 2020 in U.S. Appl. No. 15/803,480.

(Continued)

*Primary Examiner* — Galen H Hauth
(74) *Attorney, Agent, or Firm* — McGinn I.P. Law Group, PLLC.

(57) ABSTRACT

A molded product production system includes a powdery material mixing and feeding device configured to feed mixed powdery materials including at least two types of powdery materials, a filler configured to fill, with the mixed powdery materials fed by the powdery material mixing and feeding device, a die bore of a compression-molding machine, a sensor configured to measure a mixing degree of the mixed powdery materials fed by the powdery material mixing and feeding device, and a molded product removal mechanism configured to distinguish a molded product obtained by compression molding mixed powdery materials having a mixing degree measured by the sensor out of a predetermined range from a molded product obtained by compression molding mixed powdery materials having a mixing degree within the predetermined range.

20 Claims, 16 Drawing Sheets

(51) Int. Cl.
*B30B 11/08* (2006.01)
*A61K 9/20* (2006.01)
*B01F 3/18* (2006.01)
*B01F 7/00* (2006.01)
*B01F 7/04* (2006.01)
*B01F 7/20* (2006.01)
*B01F 13/10* (2006.01)
*B01F 15/00* (2006.01)
*B29B 7/44* (2006.01)
*B29B 7/72* (2006.01)
*B29C 43/02* (2006.01)
*B29C 43/34* (2006.01)
*B29K 105/00* (2006.01)

(52) U.S. Cl.
CPC ...... *B01F 7/00133* (2013.01); *B01F 7/00275* (2013.01); *B01F 7/00316* (2013.01); *B01F 7/04* (2013.01); *B01F 7/20* (2013.01); *B01F 13/1027* (2013.01); *B01F 15/00207* (2013.01); *B29B 7/44* (2013.01); *B29B 7/726* (2013.01); *B29C 43/02* (2013.01); *B29C 43/34* (2013.01); *B30B 11/08* (2013.01); *B30B 15/26* (2013.01); *B01F 2215/0032* (2013.01); *B29C 2043/585* (2013.01); *B29K 2105/251* (2013.01)

(56) References Cited

U.S. PATENT DOCUMENTS

| | | |
|---|---|---|
| 3,044,139 A | 7/1962 | Morton |
| 3,176,466 A | 4/1965 | Pinsenschaum |
| 3,191,502 A | 6/1965 | Pinsenschaum |
| 3,193,377 A | 7/1965 | Guseman |
| 3,316,339 A | 4/1967 | Breneman |
| 4,030,868 A | 6/1977 | Williams |
| 4,206,047 A | 6/1980 | Mandt |
| 4,238,431 A | 12/1980 | Stuben et al. |
| 4,368,165 A | 1/1983 | Bergendahl |
| 4,695,414 A | 9/1987 | Forslund et al. |
| 5,039,294 A | 8/1991 | Gautier et al. |
| 5,152,215 A | 10/1992 | Wetzel |
| 5,251,545 A | 10/1993 | Wetzel |
| 5,288,440 A | 2/1994 | Katagiri et al. |
| 5,470,004 A | 11/1995 | Mineki |
| 5,580,586 A | 12/1996 | Yokoyama |
| 5,838,571 A | 11/1998 | Lewis |
| 6,368,094 B1 | 4/2002 | Dennis et al. |
| 6,490,035 B1 | 12/2002 | Folestad et al. |
| 7,137,717 B2 | 11/2006 | Ohashi |
| 8,078,329 B2 | 12/2011 | Boeckx et al. |
| 8,568,630 B2 | 10/2013 | Herrmann et al. |
| 9,713,575 B2 | 7/2017 | Boeckx et al. |
| 10,016,340 B2 | 7/2018 | Boeckx et al. |
| 10,449,701 B2 | 10/2019 | Kitamura et al. |
| 2004/0012781 A1* | 1/2004 | Gehrlein ............ G01N 21/3563 356/328 |
| 2004/0056375 A1 | 3/2004 | Bubb |
| 2004/0156940 A1 | 8/2004 | Noack |
| 2005/0184435 A1* | 8/2005 | Hinzpeter ............ B30B 11/005 264/409 |
| 2005/0200038 A1* | 9/2005 | Vogeleer ............ B30B 11/005 264/40.1 |
| 2005/0241721 A1 | 11/2005 | Ritz et al. |
| 2008/0020082 A1 | 1/2008 | Plucinski et al. |
| 2009/0115059 A1 | 5/2009 | Kimura et al. |
| 2009/0115090 A1 | 5/2009 | Dukler et al. |
| 2010/0078841 A1 | 4/2010 | Herrmann et al. |
| 2010/0094449 A1* | 4/2010 | Boeckx .................. B07C 5/363 700/110 |
| 2011/0001253 A1 | 1/2011 | Isozumi |
| 2011/0024937 A1 | 2/2011 | Dukler et al. |
| 2011/0110810 A1 | 5/2011 | Burke |
| 2012/0061869 A1* | 3/2012 | Boeckx ..................... A61J 3/10 264/40.1 |
| 2014/0035203 A1 | 2/2014 | Oneda et al. |
| 2016/0243781 A1* | 8/2016 | Vandenbroucke ...... B30B 11/08 |
| 2016/0310365 A1 | 10/2016 | Boeckx et al. |
| 2016/0361885 A1 | 12/2016 | Oyama et al. |
| 2017/0282421 A1 | 10/2017 | Kitamura et al. |

FOREIGN PATENT DOCUMENTS

| | | |
|---|---|---|
| JP | 2008-183168 A | 8/2008 |
| JP | 2011-156576 A | 8/2011 |
| JP | 2014-221343 A | 11/2014 |
| KR | 2010-0127937 A | 12/2010 |
| KR | 10-1500597 B1 | 3/2015 |
| WO | WO 00/07705 A1 | 2/2000 |
| WO | WO 2010/128359 | 11/2010 |

OTHER PUBLICATIONS

Communication Pursuant to Rule 114(2) EPC, dated Oct. 9, 2019, in European Application No. 16202602.5.

Levin, M., "tablet press instrumentation" from the Encyclopeda of Pharmaceutical Technology, Marcel Dekker, Inc., New York, 2002 DOI: 10.108/E-EPT 120012030, pp. 1-26.

Marcel Dekker, Inc., New York, 2002.

Ward, Howard W., et al. "Monitoring blend potency in a tablet press feed frame using near infrared spectroscopy", Journal of Pharmaceutical and Biomedical Analysis 80 (2013) 18-23.

* cited by examiner

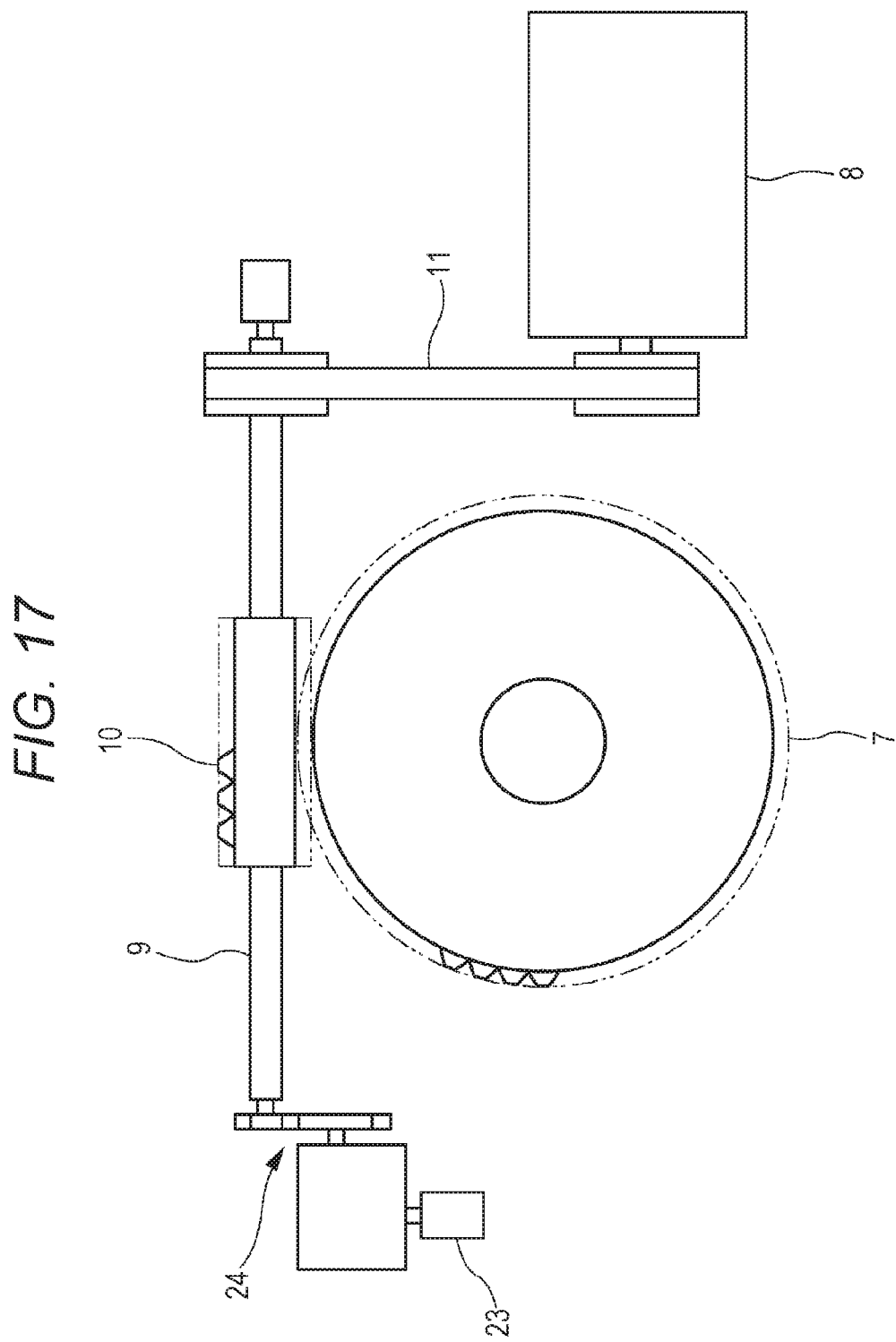

MOLDED PRODUCT PRODUCTION SYSTEM

BACKGROUND

To date, a tablet of a pharmaceutical product or the like has typically been produced by forming an intermediate product in each of the individualized processes of granulating, drying, grading, and mixing, and obtaining a tablet in the final process of compression molding (i.e., tableting).

Production according to such a batch method includes several halfway scaling-up processes in order to enlarge a small compression-molding machine for research and development to a large compression-molding machine for commercial use. There is also a need to conduct verification experiments for such scaling-up, which will increase the frequency of using a raw material of powdery material and may need enormous costs.

Moreover, the batch method includes standby periods between the processes and thus has difficulty in timely feeding an intermediate product. The batch method also needs facility design for each of the processes and occupation of a large space. Specifically, each of the processes needs a separate chamber and delivery by a worker of an intermediate product to a chamber for the subsequent process.

In view of this, there is a demand for continuously conducting the processes unlike in the batch method. Such continuous conduct of the processes needs prompt monitoring.

JP 2008-183168 A discloses a volumetric feeding device and an in-line mixer, and describes a sensor configured to promptly check a mixed state of powdery materials prior to tableting. The mixed state is, however, monitored only in a pipe. Such a configuration merely achieves removal of a defective tableted product, alert issue, or operation suspension in a case where the powdery materials have a mixing degree out of a predetermined range. Furthermore, it is difficult to specify a tablet made of the mixed powdery materials having a mixing degree out of the predetermined range.

JP 2014-221343 A discloses a tablet production module and a method of continuously producing tablets, and describes an analytical sensor. JP 2014-221343 A, however, fails to clarify how to specifically configure the tablet production module and how to monitor.

SUMMARY OF THE INVENTION

It is an exemplary feature of the present invention to appropriately monitor a mixing degree of mixed powdery materials and maintain quality of a molded product obtained by compression molding the mixed powdery materials.

The invention exemplarily provides a molded product production system including a powdery material mixing and feeding device configured to feed mixed powdery materials including at least two types of powdery materials, a filler configured to fill, with the mixed powdery materials fed by the powdery material mixing and feeding device, a die bore of a compression-molding machine configured to compress a powdery material to mold a molded product, a sensor configured to measure a mixing degree of the mixed powdery materials fed by the powdery material mixing and feeding device, and a molded product removal mechanism configured to distinguish a molded product obtained by compression molding mixed powdery materials having a mixing degree measured by the sensor out of a predetermined range from a molded product obtained by compression molding mixed powdery materials having a mixing degree within the predetermined range. Such a system achieves monitoring the mixing degree of the mixed powdery materials of raw materials for the molded product, and easily finding whether or not the mixing degree of the mixed powdery materials is within the predetermined range. The molded product of the mixed powdery materials having a mixing degree out of the predetermined range can be removed from the molded product of the mixed powdery materials having a mixing degree within the predetermined range.

The molded product production system including the sensor disposed at the filler or between the powdery material mixing and feeding device and the filler can reliably monitor the mixing degree of the mixed powdery materials filled by the filler in the die bore of the compression-molding machine.

The molded product removal mechanism can be configured to sample the molded product. The molded product removal mechanism functions also as a molded product sampling device in this case.

The invention further provides a method of producing a compression-molded product with a compression-molding machine from mixed powdery materials including at least two types of powdery materials. The method includes mixing the at least two types of powdery material, measuring a mixing degree of the mixed powdery materials with a sensor, filling a die bore of the compression-molding machine with the mixed powdery materials, compression molding, after the filling, the mixed powdery materials filled in the die bore, with an upper punch and a lower punch of the compression-molding machine, and removing a molded product by distinguishing, in the compression-molding machine, a molded product obtained by compression molding mixed powdery materials having a mixing degree measured by the sensor out of a predetermined range from a molded product obtained by compression molding mixed powdery materials having a mixing degree within the predetermined range. Such a method may achieve promptly monitoring the mixing degree of the mixed powdery materials and continuously conducting mixing to compression molding (e.g., tableting) unlike in the conventional batch method. Furthermore, the molded product of the mixed powdery materials having a mixing degree out of the predetermined range can be removed from the molded product of the mixed powdery materials having a mixing degree within the predetermined range.

A powdery material according to an exemplary aspect of the invention refers to an aggregate of minute solids and conceptually includes an aggregate of particles such as so-called granules and an aggregate of powder smaller than such particles. Examples of the powdery material include a lubricant such as magnesium stearate. Powdery materials subjected to the mixing by the powdery material mixing and feeding device are referred to as mixed powdery materials for convenient description. Examples of the powdery material include the mixed powdery materials.

The powdery materials are categorized into a powdery material containing a principal agent, an excipient, a binder, a disintegrant, a lubricant, a stabilizer, a preservative, and the like, and conceptually include mixed powdery materials.

The invention may achieve appropriately monitoring a mixing degree of mixed powdery materials and maintaining quality of a molded product obtained by compression molding the mixed powdery materials.

BRIEF DESCRIPTION OF THE DRAWINGS

The exemplary aspects of the invention will be better understood from the following detailed description of the exemplary embodiments of the invention with reference to the drawings:

FIG. 17 is a plan view of a main part including a mounting position of a rotary encoder in the compression-molding machine according to the exemplary embodiment.

DETAILED DESCRIPTION OF AN EXEMPLARY EMBODIMENT

An exemplary embodiment of the invention will now be described with reference to the drawings. A compression-molding machine according to the exemplary embodiment is of a rotary type. An outline of the entire rotary compression-molding machine will initially be described.

Figure 1:
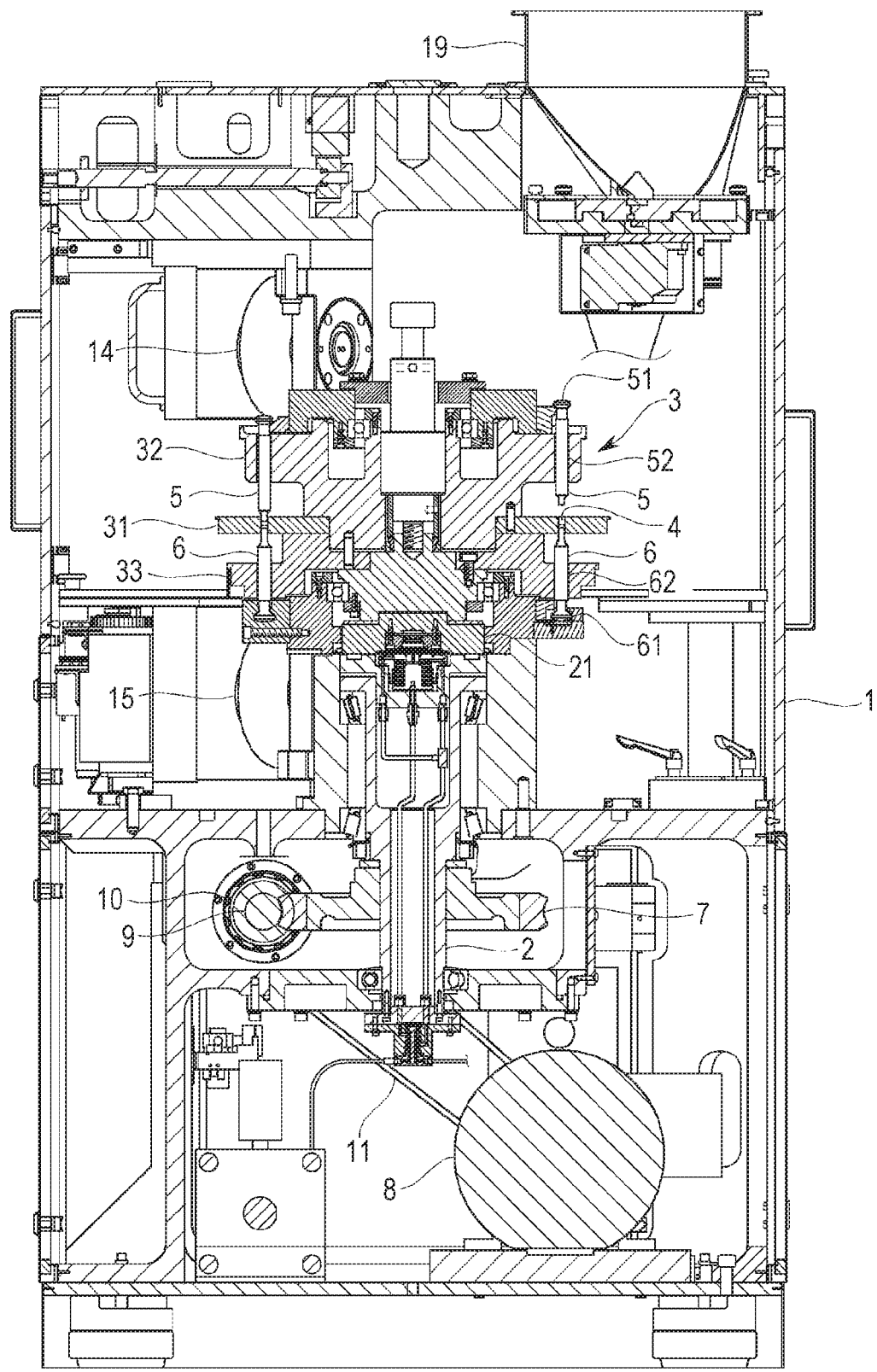
FIG. 1 is a side sectional view of a compression-molding machine according to an exemplary embodiment of the invention.

As shown exemplarily in FIG. 1, the compression-molding machine includes a frame 1 accommodating an upright shaft 2 that functions as a rotary shaft, and a turret 3 that is attached to a connection portion 21 disposed at the top of the upright shaft 2. A worm wheel 7 is attached to the lower end of the upright shaft 2. The worm wheel 7 meshes with a worm gear 10. The worm gear 10 is fixed to a gear shaft 9 that is driven by a motor 8. Drive power outputted from the motor 8 is transmitted to the gear shaft 9 by way of a belt 11, so as to rotate the upright shaft 2 by way of the worm gear 10 and the worm wheel 7. Rotation of the upright shaft 2 causes rotation of the turret 3 and upper and lower punches 5 and 6.

Figure 2:
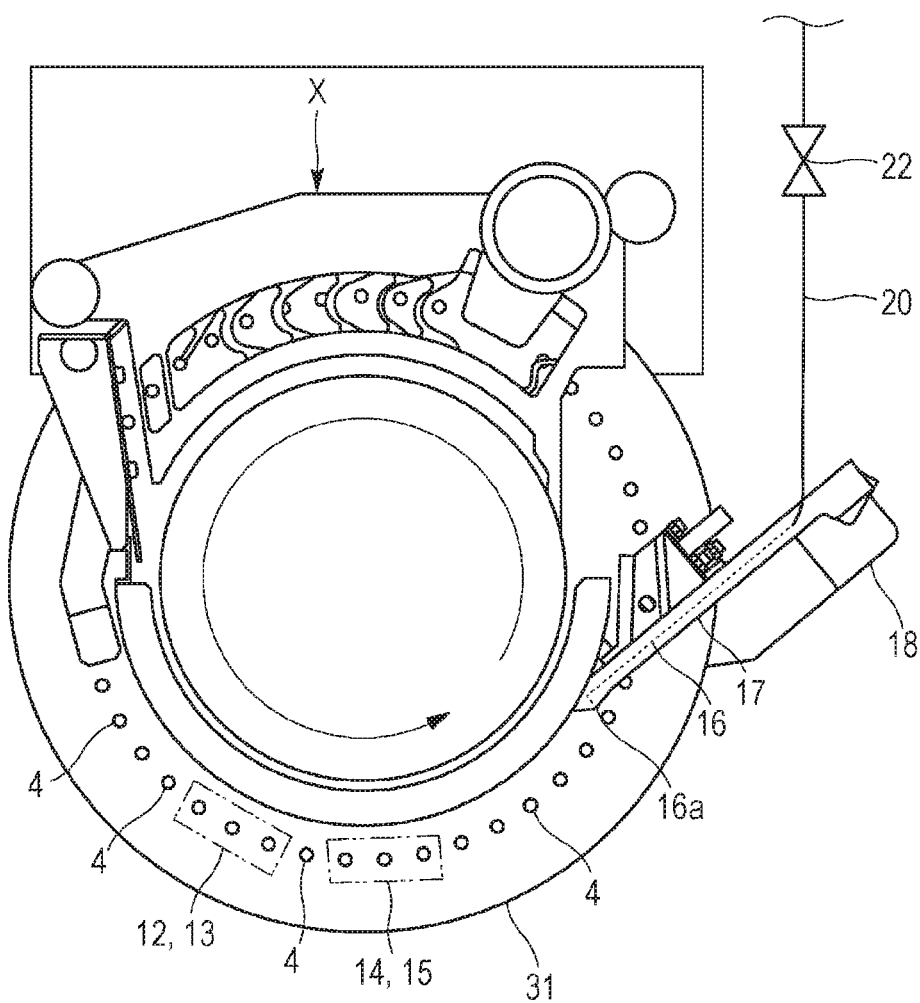
FIG. 2 is a plan view of a main part of the compression-molding machine according to the exemplary embodiment.

The turret 3 horizontally rotates about the upright shaft 2, and more specifically, spins. The turret 3 includes a table (e.g., a die disc) 31, an upper punch retaining portion 32, and a lower punch retaining portion 33. As shown in exemplary FIG. 2, the table 31 has a substantially circular disc shape, and has a plurality of die bores 4 that is disposed in an outer circumferential portion and is aligned in a direction of rotation at predetermined intervals. Each of the die bores 4 vertically penetrates the table 31. The table 31 can alternatively include a plurality of divided plates. Instead of the die bores 4 formed directly in the table 31, a die member including the die bores 4 can be attached to the table 31.

The upper and lower punches 5 and 6 are disposed above and below each of the die bores 4 and are individually vertically slidable along the die bores 4. The upper punch retaining portion 32 retains upper punch trunks 52 while the lower punch retaining portion 33 retains lower punch trunks 62. The upper punches 5 each have a tip 53 that enters and exits the corresponding one of the die bores 4. The lower punches 6 each have a tip 63 that is kept inserted in corresponding one of the die bores 4. The upper and lower punches 5 and 6 horizontally rotate about the upright shaft 2 along with the turret 3, more specifically, revolve.

As shown exemplarily in FIG. 17, the gear shaft 9 has an end connected, via a reduction gear 24, with a rotary encoder 23 configured to detect a rotation angle and rotational speed of the gear shaft 9 as well as (the table 31, the die bores 4, and the punches 5 and 6) of the turret 3. The rotary encoder 23 outputs a pulse signal every time the gear shaft 9 rotates by a predetermined angle. Upon receipt of a train of the pulse signals, a controller C included in a molded product production system is configured to detect the rotation angle and the rotational speed of the turret 3 (i.e., find a current position of each of the die bores 4 on the table 31). The reduction gear 24 reduces the rotational speed of the gear shaft 9 to be adapted to an input speed of the rotary encoder 23 and transmits the reduced rotational speed to the rotary encoder 23.

A feeder X functioning as a filler is provided to fill the die bores 4 of the turret 3 with a powdery material. Examples of the feeder X include an agitated feeder and a gravity feeder. The feeder X can be any one of these feeders. A powdery material is fed to the feeder X from a powdery material feed passage 191 functioning as a discharger M6 of a powdery material mixing degree measurement device M. A buffer tank 19 is provided to feed a feeding unit M5 of the powdery material mixing degree measurement device M with a powdery material.

Figure 3:
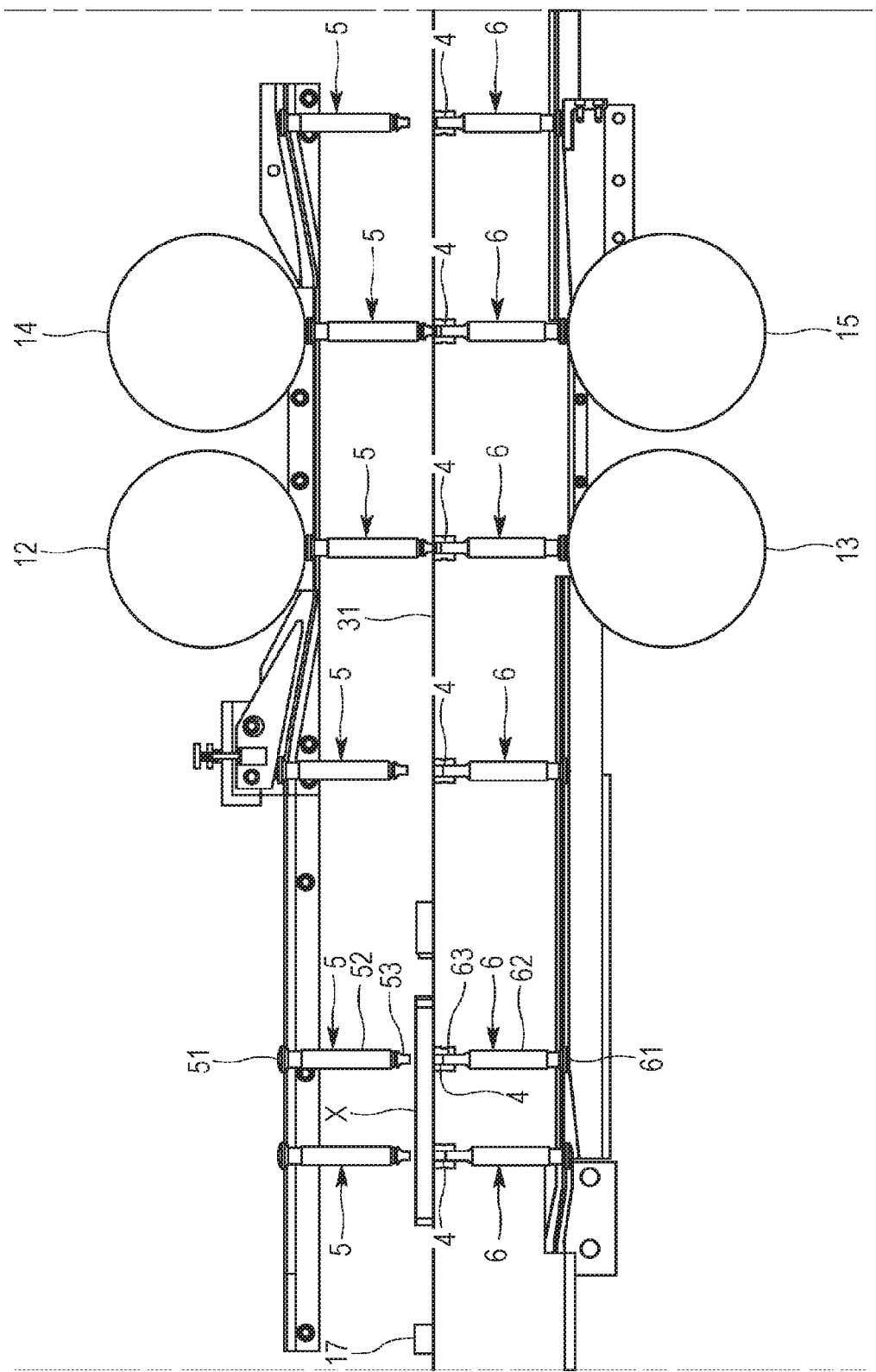
FIG. 3 is a cylindrical view of the compression-molding machine according to the exemplary embodiment.

As shown exemplarily in FIG. 3, a preliminary compression upper roll 12, a preliminary compression lower roll 13, a substantial compression upper roll 14, and a substantial compression lower roll 15 are disposed on orbits of the upper and lower punches 5 and 6 that revolve about the upright shaft 2. The preliminary compression upper roll 12 and the preliminary compression lower roll 13, as well as the substantial compression upper roll 14 and the substantial compression lower roll 15, are respectively paired in the vertical direction so as to sandwich the upper and lower punches 5 and 6. The preliminary compression upper roll 12 and the substantial compression upper roll 14 each press a head 51 of each of the upper punches 5, and the preliminary compression lower roll 13 and the substantial compression lower roll 15 each press a head 61 of each of the lower punches 6. The preliminary compression upper roll 12 and the preliminary compression lower roll 13, as well as the substantial compression upper roll 14 and the substantial compression lower roll 15, bias the upper and lower punches 5 and 6 to come closer to each other, so that end surfaces of the tips 53 and 63 compress from above and below a powdery material filled in the die bores 4.

The upper and lower punches 5 and 6 have the heads 51 and 61 pressed by the rolls 12, 13, 14, and 15, and the trunks 52 and 62 smaller in diameter than the heads 51 and 61. The upper punch retaining portion 32 of the turret 3 vertically slidably retains the trunks 52 of the upper punches 5, whereas the lower punch retaining portion 33 vertically slidably retains the trunks 62 of the lower punches 6. The tips 53 and 63 of the trunks 52 and 62 are thinner than the remaining portions and are substantially equal in diameter to an inner diameter of the die bores 4 so as to be inserted to the die bores 4. The punches 5 and 6 revolve to cause the rolls 12, 13, 14, and 15 to come closer to the heads 51 and 61 of the punches 5 and 6. The rolls 12, 13, 14, and 15 come into contact with the heads 51 and 61 so as to step thereonto. The rolls 12, 13, 14, and 15 further press the upper punches 5 downward and press the lower punches 6 upward. While the rolls 12, 13, 14, and 15 are in contact with flat surfaces of the punches 5 and 6, the punches 5 and 6 keep applying required pressure to a powdery material in the die bores 4.

A molded-product collector is disposed downstream, in the direction of rotation of the turret 3 and the punches 5 and 6, of the position where the substantial compression upper roll 14 and the substantial compression lower roll 15 apply pressure. This molded-product collector includes a guide member 17 configured to guide a molded product pushed out of each of the die bores 4. The guide member 17 extends to have a proximal end located at a molded-product collecting position 18 and a distal end located closer to the center of the table 31 than a rotation locus of the die bores 4. A molded product pushed out of each of the die bores 4 by the corresponding lower punch 6 comes into contact with the guide member 17 and moves toward the molded-product collecting position 18.

A production process of a molded product will be described below. As shown exemplarily in FIG. 3, the lower punch 6 initially descends and the feeder X fills, with a powdery material (e.g., mixed powdery materials), the die bore 4 into which the tip 63 of the lower punch 6 is inserted (i.e., filling). The lower punch 6 subsequently ascends such that the die bore 4 is filled with a required amount of the powdery material (e.g., mixed powdery materials), and the powdery material overflowing the die bore 4 is leveled.

The upper punch 5 then descends, and the preliminary compression upper roll 12 and the preliminary compression lower roll 13 press the head 51 of the upper punch 5 and the head 61 of the lower punch 6, such that the tips 53 and 63 of the punches 5 and 6 preliminarily compress the powdery material in the die bore 4. The substantial compression upper roll 14 and the substantial compression lower roll 15 subsequently press the head 51 of the upper punch 5 and the head 61 of the lower punch 6, such that the tips 53 and 63 of the punches 5 and 6 substantially compress the powdery material in the die bore 4 (i.e., compression molding).

The lower punch 6 then ascends until the upper end surface of the tip 63 of the lower punch 6 substantially reaches the level of the upper end of the die bore 4, i.e. the top surface of the table 31, and pushes a molded product out of the die bore 4 onto the surface of the turret 3. The molded product pushed out of the die bore 4 is brought into contact with the guide member 17 by rotation of the turret 3, and moves along the guide member 17 to the molded-product collecting position 18.

The molded-product collector of the compression-molding machine has a molded-product removal mechanism W configured to select a specific molded product such as a sampled product or a defective product from among molded-products collected at the molded-product collecting position 18. Specifically, the guide member 17 is provided therein with an air passage 16 for a pressurized air flow, and the air passage 16 has a distal end functioning as an air spray nozzle 16a opened outward in the radial direction of the turret 3. A flow passage 20 connects an air feed source (not shown) such as a pump configured to feed pressurized air and the air passage 16, and a control valve 22 is disposed on the flow passage 20 to open and close the flow passage 20. An example of the control valve 22 include an electromagnetic solenoid configured to open in accordance with a control signal transmitted from a controller C or the like.

If the control valve 22 is opened when a specific molded product pushed out of the die bore 4 passes by the air spray nozzle 16a before contacting the guide member 17, then the air spray nozzle 16a discharges pressurized air fed from the air feed source through the flow passage 20 and the air passage 16 in the guide member 17. The discharged air blows the specific molded product outward from the table 31. The blown molded product will not reach the molded-product collecting position 18 ahead of the guide member 17. As described above, the molded-product removal mechanism W in the compression-molding machine includes the passages 16 and 20 for air fed from the air feed source, the spray nozzle 16a, and the control valve 22.

The molded-product removal mechanism W is also configured to sample a tableted molded product.

A powdery material mixing and feeding device Z configured to feed the buffer tank 19 with a powdery material will be described below. As shown exemplarily in FIGS. 4 and 5, the powdery material mixing and feeding device Z according to the exemplary embodiment includes three measuring feeders Z1 (Z1a, Z1b, and Z1c). The number of the measuring feeders Z1 changes depending on the number of types of powdery materials to be mixed. The powdery material mixing and feeding device Z can include two, four, or more measuring feeders Z1 with no particular limitation in the number thereof.

The first to third measuring feeders Z1a to Z1c according to the exemplary embodiment measure and feed different types of powdery materials. These measuring feeders Z1a to Z1c can alternatively measure and feed a single type of a powdery material. In the exemplary embodiment, the first measuring feeder Z1a, the second measuring feeder Z1b, and the third measuring feeder Z1c measure and feed a principal agent, a powdery material of an excipient like lactose, or the like, and a lubricant, respectively.

Figure 4:
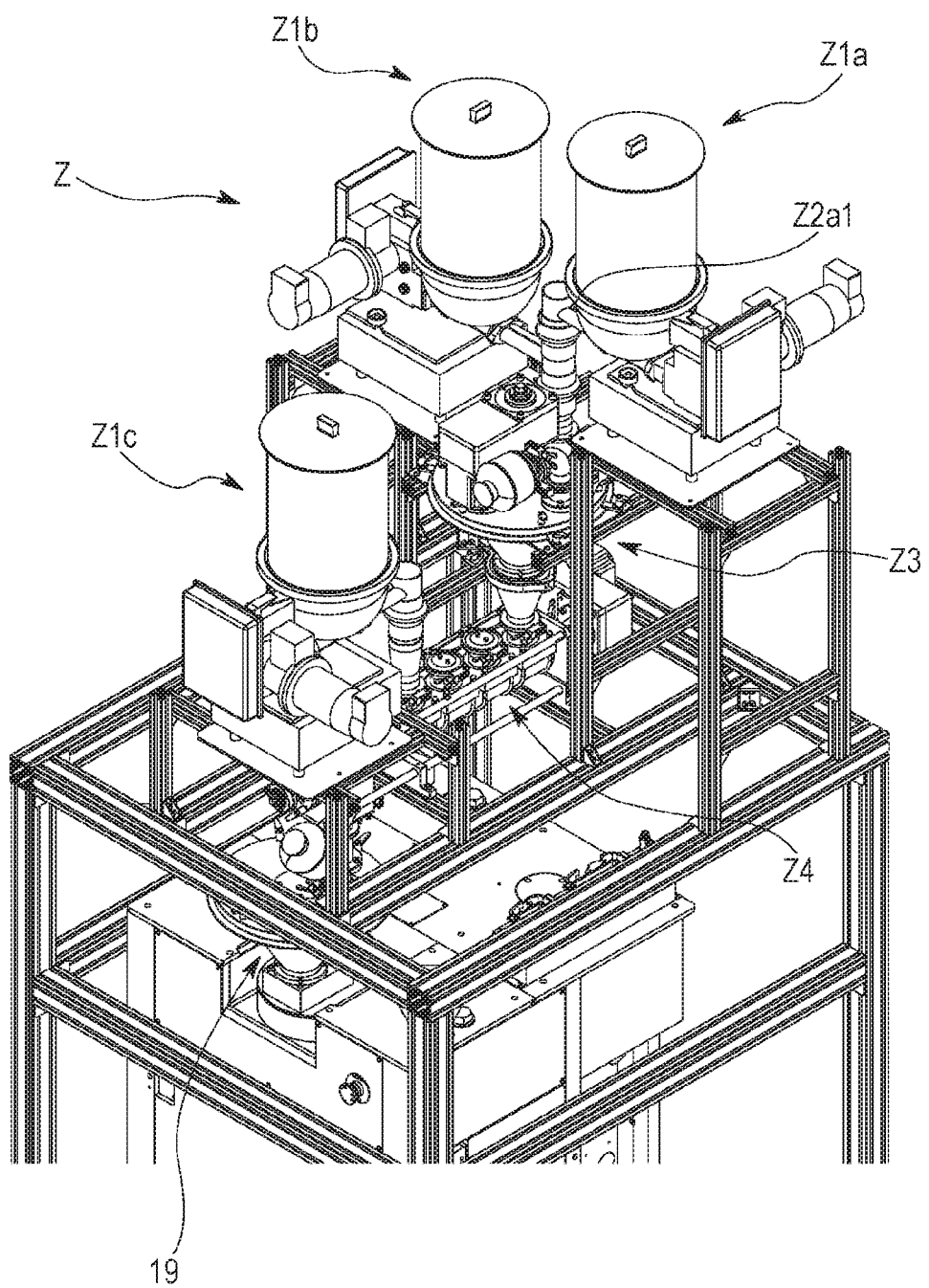
FIG. 4 is a perspective view of a powdery material mixing and feeding device according to the exemplary embodiment.
Figure 5:
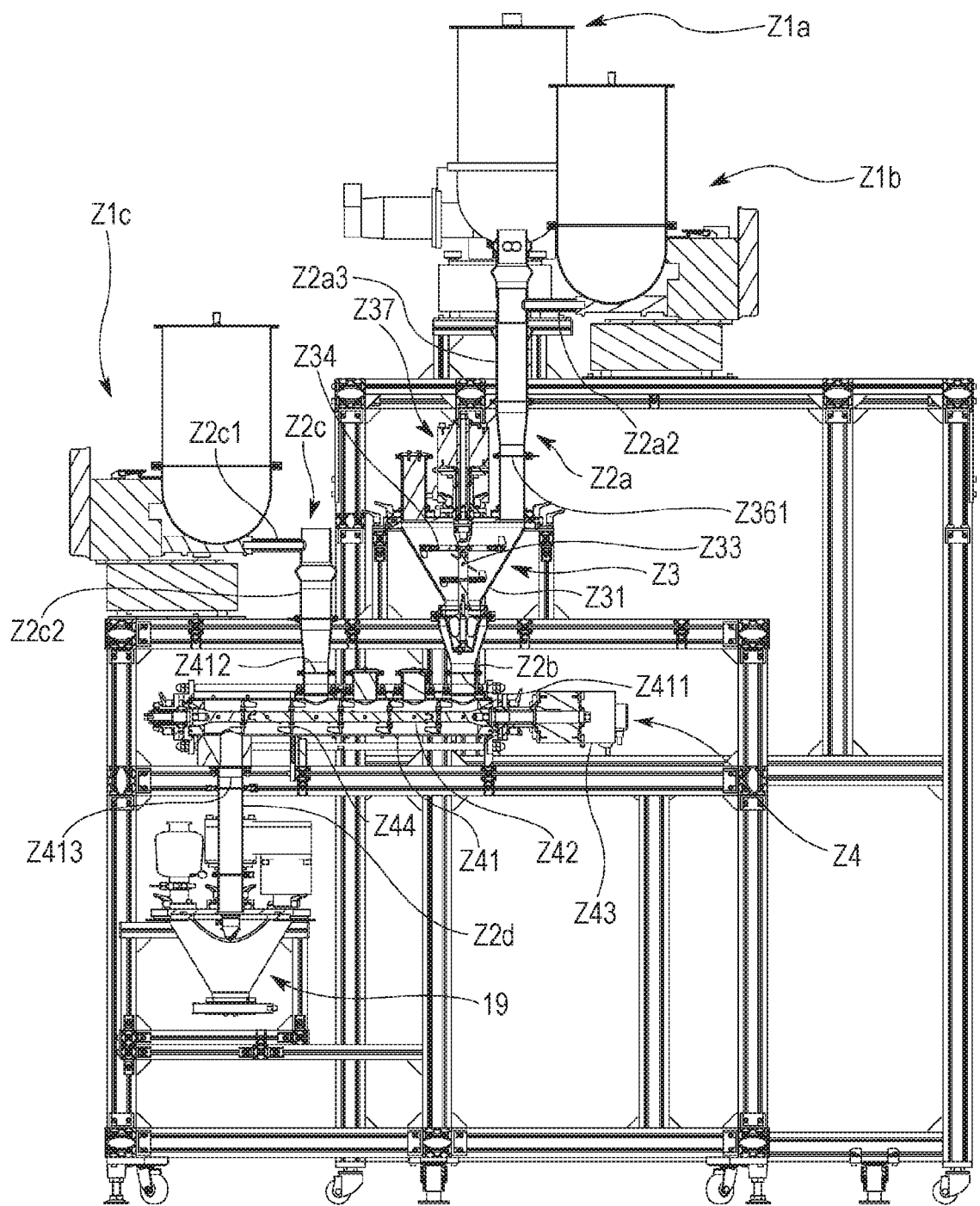
FIG. 5 is a side view of the powdery material mixing and feeding device according to the exemplary embodiment.
Figure 6:
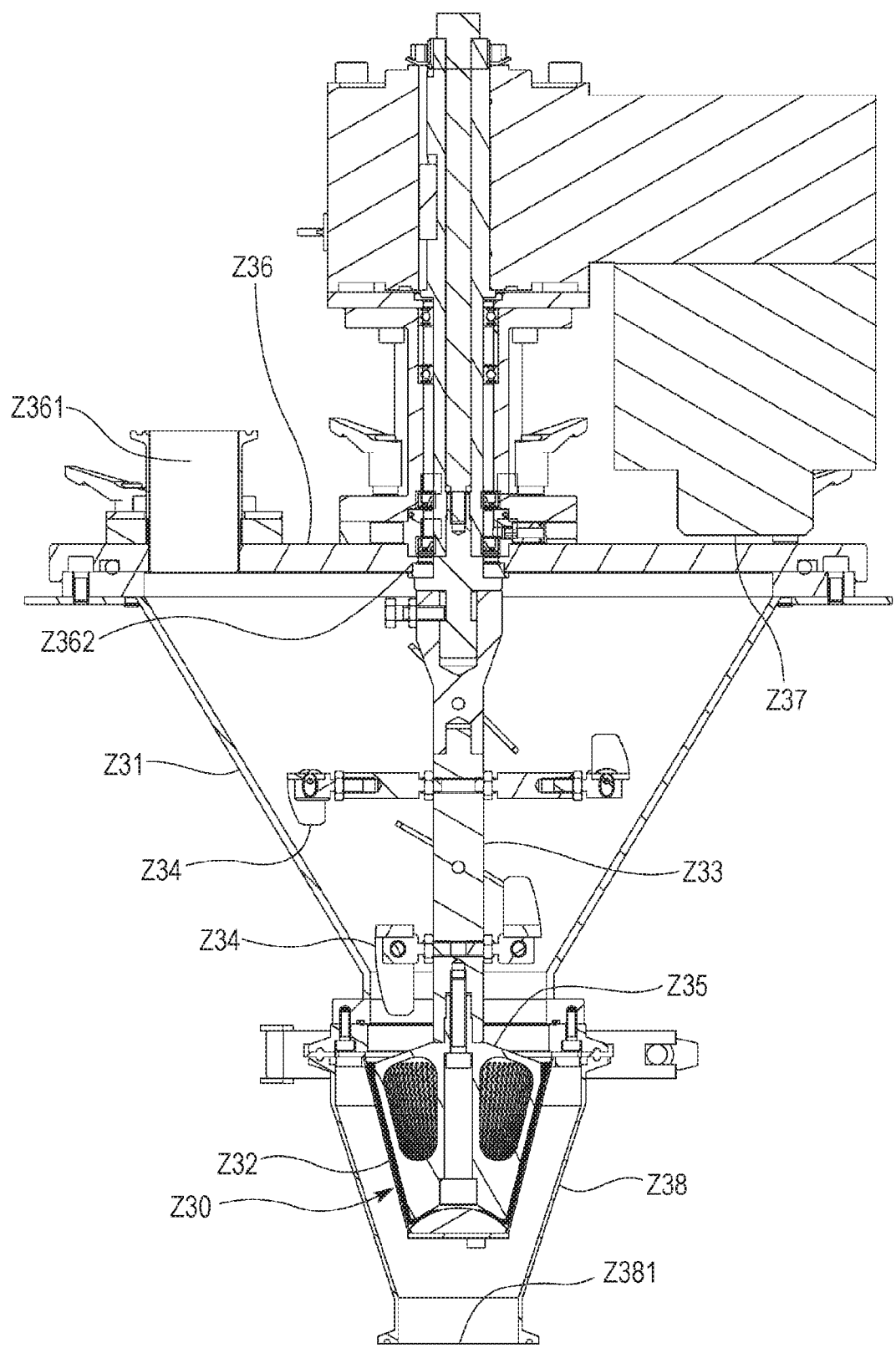
FIG. 6 is a side sectional view of a vertical mixer included in the powdery material mixing and feeding device according to the exemplary embodiment.

As shown exemplarily in FIGS. 4 and 5, the powdery material mixing and feeding device Z includes the first measuring feeder Z1a, the second measuring feeder Z1b, a vertical mixer Z3 (i.e., a first mixer), a first connecting pipe Z2a connecting the measuring feeders Z1 (Z1a and Z1b) and the vertical mixer Z3, a horizontal mixer Z4 (e.g., a second mixer), a second connecting pipe Z2b connecting the vertical mixer Z3 and the horizontal mixer Z4, a third connecting pipe Z2c connecting the third measuring feeder Z1c and the horizontal mixer Z4, and a fourth connecting pipe Z2d connecting the horizontal mixer Z4 and the buffer tank 19. FIG. 4 is a perspective view of a state where the powdery material mixing and feeding device Z is attached to the compression-molding machine. FIG. 5 is a side view of the powdery material mixing and feeding device Z. The measuring feeders (e.g., Z1a, Z1b, and Z1c) can be modified in terms of their disposition, shapes, and the like, and are not limited to the aspect shown in FIGS. 4 and 5.

The first measuring feeder Z1a and the second measuring feeder Z1b measure the powdery materials, namely, the principal agent and the excipient or the like, respectively, and feed the first connecting pipe Z2a with the powdery materials simultaneously. The third measuring feeder Z1c measures the powdery material, namely, the lubricant, and feeds the third connecting pipe Z2c with the powdery material simultaneously (i.e., measuring and feeding). These measuring feeders Z1 are configured in accordance with the known loss in weight system (e.g., a loss integrated value system), and each conducts feedback control of causing weight of a powdery material discharged from the feeder Z1 to be constantly measured with a gravimetric sensor, comparing to find whether or not the weight transitions to achieve a set target discharge flow rate, and increasing or decreasing a discharge rate of the feeder Z1 to reduce a difference therebetween. Measuring the powdery materials to be fed and feeding the connecting pipes Z2a and Z2c with the powdery materials stabilizes contents of the principal agent and the like in a molded product.

As described earlier, the first connecting pipe Z2a connects the first measuring feeder Z1a and the second measuring feeder Z1b to the vertical mixer Z3, and feeds the vertical mixer Z3 with the principal agent discharged from the first measuring feeder Z1a and the excipient or the like discharged from the second measuring feeder Z1b. The second connecting pipe Z2b connects the vertical mixer Z3 and the horizontal mixer Z4, and feeds the horizontal mixer Z4 with the mixed powdery materials of the principal agent and the excipient discharged from the vertical mixer Z3. The third connecting pipe Z2c connects the third measuring feeder Z1c and the horizontal mixer Z4, and feeds the horizontal mixer Z4 with the lubricant discharged from the third measuring feeder Z1c. The fourth connecting pipe Z2d connects the horizontal mixer Z4 and the buffer tank 19, and feeds the buffer tank 19 with the mixed powdery materials of the principal agent, the excipient, and the lubricant discharged from the horizontal mixer Z4.

More specifically, the first connecting pipe Z2a includes a first branch pipe Z2a1 connected with the first measuring feeder Z1a, a second branch pipe Z2a2 connected with the second measuring feeder Z1b, and a main pipe Z2a3 connected with the first branch pipe Z2a1 and the second branch pipe Z2a2. The main pipe Z2a3 has a lower end connected with the vertical mixer Z3. The vertical mixer Z3 thus mixes the powdery materials measured and fed by the first measuring feeder Z1a and the second measuring feeder Z1b (i.e., first mixing).

The second connecting pipe Z2b, the third connecting pipe Z2c, and the fourth connecting pipe Z2d will be described later.

As shown exemplarily in FIGS. 5 to 8, the vertical mixer Z3 includes a lid Z36 having a feed port Z361 for a powdery material, a first case Z31 disposed below the lid Z36 and having a funnel shape, an agitation shaft Z33 disposed substantially in the center of the first case Z31 and configured to spin, an agitating rotor Z34 (i.e., a first mixing member) attached to the agitation shaft Z33, a motor Z37 configured to rotate (i.e., spin) the agitation shaft Z33, a powdery material passing member Z32 disposed below the first case Z31 and having a plurality of bores Z321, an auxiliary rotor Z35 (i.e., a first mixing member) configured to facilitate a powdery material to pass through the bores Z321 of the powdery material passing member Z32, and a second case Z38 covering the powdery material passing member Z32. The agitating rotor Z34 and the auxiliary rotor Z35 each function as the first mixing member. The configuration according to the exemplary embodiment includes both the agitating rotor Z34 and the auxiliary rotor Z35, while the exemplary invention is also applicable to another configuration including only one of the agitating rotor Z34 and the auxiliary rotor Z35.

The agitation shaft Z33 of the vertical mixer Z3 is not necessarily disposed vertically but can be slanted. The vertical mixer Z3 has only to be configured to agitate and mix powdery materials while the powdery materials fed from the feed port Z361 is flowing downward.

The powdery materials fed through the feed port Z361 of the vertical mixer Z3 are mixed by rotation of the agitating rotor Z34 (i.e., first mixing). The powdery materials can alternatively be mixed by rotation of the auxiliary rotor Z35.

The lid Z36 includes the feed port Z361 and a shaft port Z362 allowing the agitation shaft Z33 to pass therethrough, and is shaped to cover an upper opening of the first case Z31. The lid Z36 is attached to the first case Z31 so as to prevent a powdery material from spilling or scattering from the first case Z31. The feed port Z361 of the lid Z36 is connected with the first connecting pipe Z2a. The powdery materials fed from the feed port Z361 into the first case Z31 are agitated and mixed by a rotation of the agitating rotor Z34 and/or the auxiliary rotor Z35. The powdery material passing member Z32 disposed at a reservoir Z30 has the plurality of bores Z321 through which the mixed powdery materials pass.

Adjustment in an amount of the powdery materials fed from the feed port Z361 or an increase in a rotational speed of the auxiliary rotor Z35 can cause the powdery materials fed from the feed port Z361 to be larger in amount than the powdery materials passing through the bores Z321. A certain amount of the powdery materials will thus remain in the reservoir Z30. Specifically, at least part of the powdery materials measured and fed by the first measuring feeder Z1a and the second measuring feeder Z1b remain in the reservoir Z30 in the vertical mixer Z3 (i.e., reserving) and is agitated by the auxiliary rotor Z35, to achieve improvement in mixing degree of the powdery materials. There can be included a plurality of feed ports Z361.

The first case Z31 has the open top and the powdery material passing member Z32 is disposed below the first case Z31. The first case Z31 according to the exemplary embodiment has the substantially funnel shape, while the first case Z31 is not limited to this shape but can have any shape if it is configured to feed the powdery material passing member Z32 with a powdery material.

The agitation shaft Z33 is disposed in the center of the first case Z31 in a plan view and is driven to rotate (i.e., spin) by the motor Z37. The agitating rotor Z34 is attached to each of the top and the center in the axial direction of the agitation shaft Z33, and the auxiliary rotor Z35 is attached to the lower end in the axial direction of the agitation shaft Z33. Rotation of the agitation shaft Z33 rotates the agitating rotors Z34 and the auxiliary rotor Z35.

Figure 8:
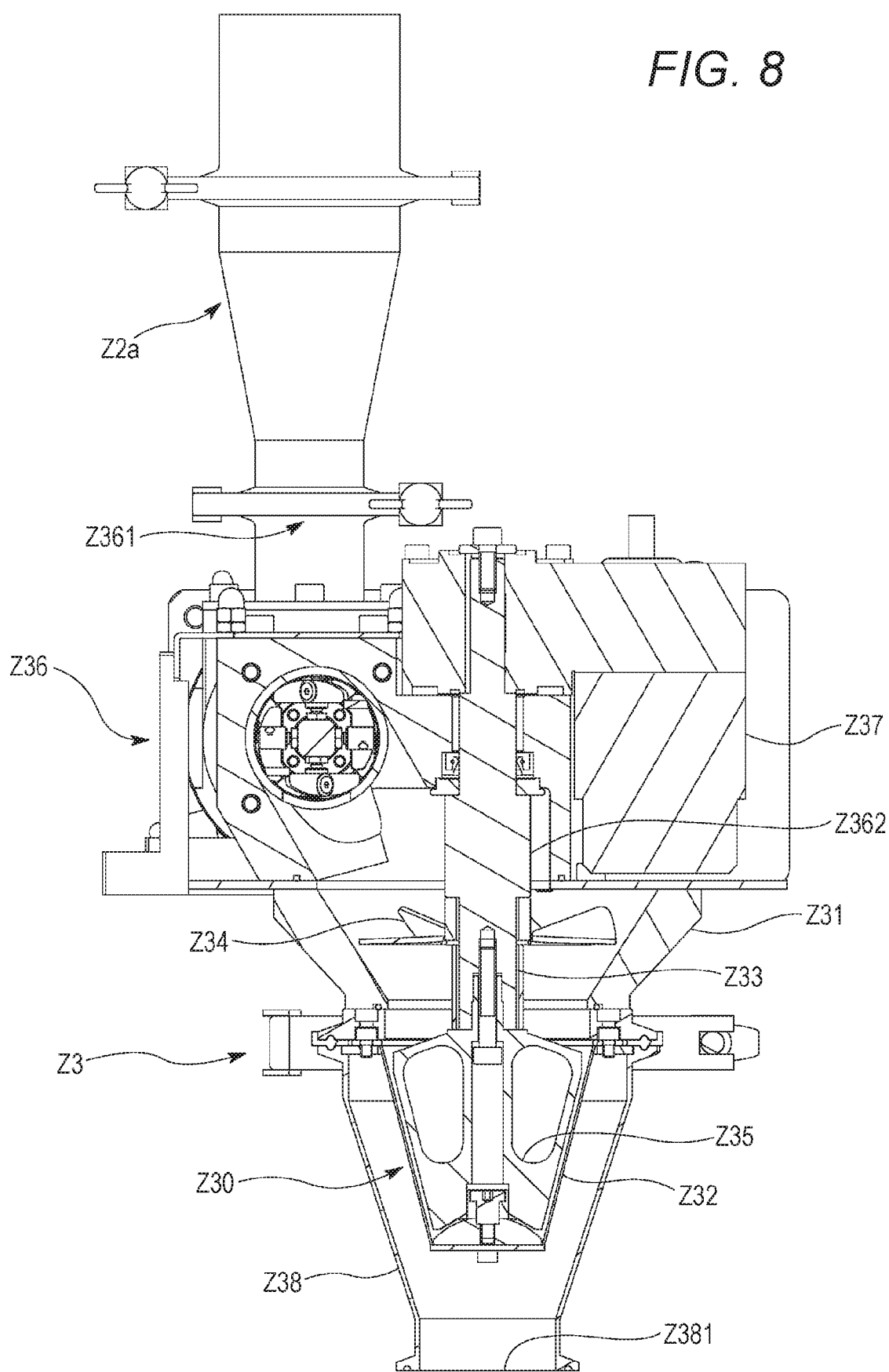
FIG. 8 is a side sectional view of another exemplary vertical mixer.

The agitating rotors Z34 (i.e., a first mixing members) agitate and mix the powdery materials fed from the feed port Z361 into the first case Z31. The agitating rotors Z34 can have any shape. The agitating rotors Z34 shown in FIGS. 5 and 6 have a rectangular distal end and are disposed at two positions on the agitation shaft Z33. The vertical mixer Z3 shown exemplarily in FIG. 8 is configured partially differently from the vertical mixer Z3 shown in FIGS. 5 and 6. The vertical mixer Z3 shown in FIG. 8 includes the agitating rotor Z34 disposed at a single position on the agitation shaft Z33 and shaped differently from the agitating rotors Z34 shown in FIGS. 5 and 6. The agitating rotors Z34 are not limited in terms of their shapes or positions to those shown exemplarily in FIGS. 5, 6, and 8.

Figure 7:
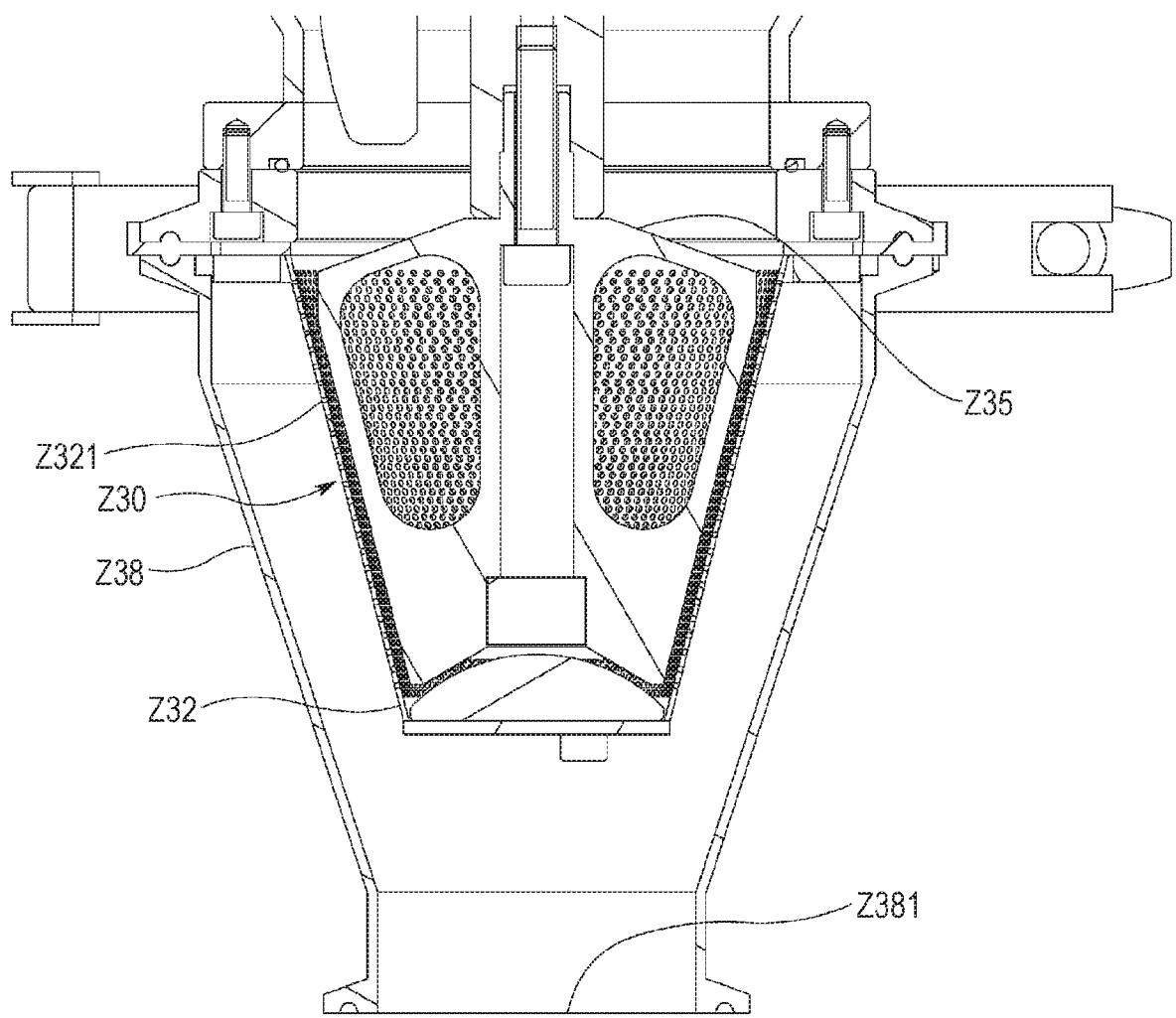
FIG. 7 is a side sectional view of an enlarged main part of the vertical mixer according to the exemplary embodiment.

As shown exemplarily in FIG. 7, the powdery material passing member Z32 at the reservoir Z30 is disposed below the first case Z31 and includes the plurality of bores Z321. The powdery material passing member Z32 is covered with the second case Z38. A powdery material passing through the bores Z321 of the powdery material passing member Z32 is discharged from a discharge port Z381 disposed at the bottom of the second case Z38. The number and the diameter of the bores Z321 are set appropriately. Such a configuration allows powdery materials to remain at the powdery material passing member Z32 and may achieve improvement in mixing degree of the powdery materials. A powdery material passing through the bores Z321 of the powdery material passing member Z32 in a first vertical mixer Z3a is fed to the horizontal mixer Z4 by way of the second connecting pipe Z2b.

The auxiliary rotor Z35 agitates a powdery material in the reservoir Z30. The auxiliary rotor Z35 is disposed in the center of the reservoir Z30 in a plan view and is attached to the lower end of the agitation shaft Z33. The auxiliary rotor Z35 according to the exemplary embodiment is shaped to follow the inner shape of the powdery material passing member Z32 and facilitates a powdery material to pass through the bores Z321. The auxiliary rotor Z35 is also configured as a type of an agitating rotor.

The vertical mixer Z3 according to the exemplary embodiment includes the agitating rotor Z34. The vertical mixer Z3 can alternatively be configured by the second case Z38, the powdery material passing member Z32, and the auxiliary rotor Z35. The second case Z38 covers the powdery material passing member Z32, has a substantially funnel shape, and has the discharge port Z381 at the bottom. The second case Z38 guides a powdery material passing through the bores Z321 of the powdery material passing member Z32 to the discharge port Z381.

The second connecting pipe Z2b connects the vertical mixer Z3 and the horizontal mixer Z4 to be described later. The second connecting pipe Z2b is connected to the bottom of the vertical mixer Z3 and the top of the horizontal mixer Z4, and feeds the horizontal mixer Z4 with the powdery materials passing through the discharge port Z381 of the vertical mixer Z3.

As shown exemplarily in FIG. 5, the horizontal mixer Z4 functioning as the second mixer includes a cylindrical case Z41, an agitation shaft Z42 disposed substantially in the center of the case Z41 and configured to spin, a motor Z43 configured to rotate (i.e., spin) the agitation shaft Z42, and an agitating rotor Z44 attached to the agitation shaft Z42 and configured to rotate to move a powdery material substantially horizontally. The horizontal mixer Z4 mixes the fed powdery materials, namely, the principal agent and the excipient or the like with the lubricant (i.e., second mixing). The case Z41 according to the exemplary embodiment does not rotate (i.e., spin), but can alternatively be configured to rotate. This may achieve further improvement in a mixing degree of the powdery materials.

The case Z41 has a top including a plurality of feed ports that allows powdery materials to be fed into the case Z41, and a discharge port Z413 that allows mixed powdery materials to be discharged from the case Z41. The configuration according to the exemplary embodiment includes two feed ports (e.g., first and second feed ports Z411 and Z412), and the second connecting pipe Z2b is connected to the first feed port Z411 of the case Z41 of the horizontal mixer Z4. The first feed port Z411 feeds the case Z41 with the mixed powdery materials of the principal agent and the excipient or the like. The agitating rotor Z44 rotates to move the mixed powdery materials fed into the case Z41 toward the discharge port Z413 of the case Z41. The second feed port Z412 feeds the lubricant from the third connecting pipe Z2c. The agitation shaft Z42 and the agitating rotor Z44 rotate to move the lubricant fed into the case Z41 toward the discharge port Z413 of the case Z41. Any of the feed ports not in use will be closed by a lid.

The discharge port Z413 is disposed at the bottom of the case Z41. The discharge port Z413 is connected with the fourth connecting pipe Z2d to be described later. The agitating rotor Z44 rotates to discharge the mixed powdery materials from the case Z41 through the discharge port Z413 to the fourth connecting pipe Z2d.

Figure 9:
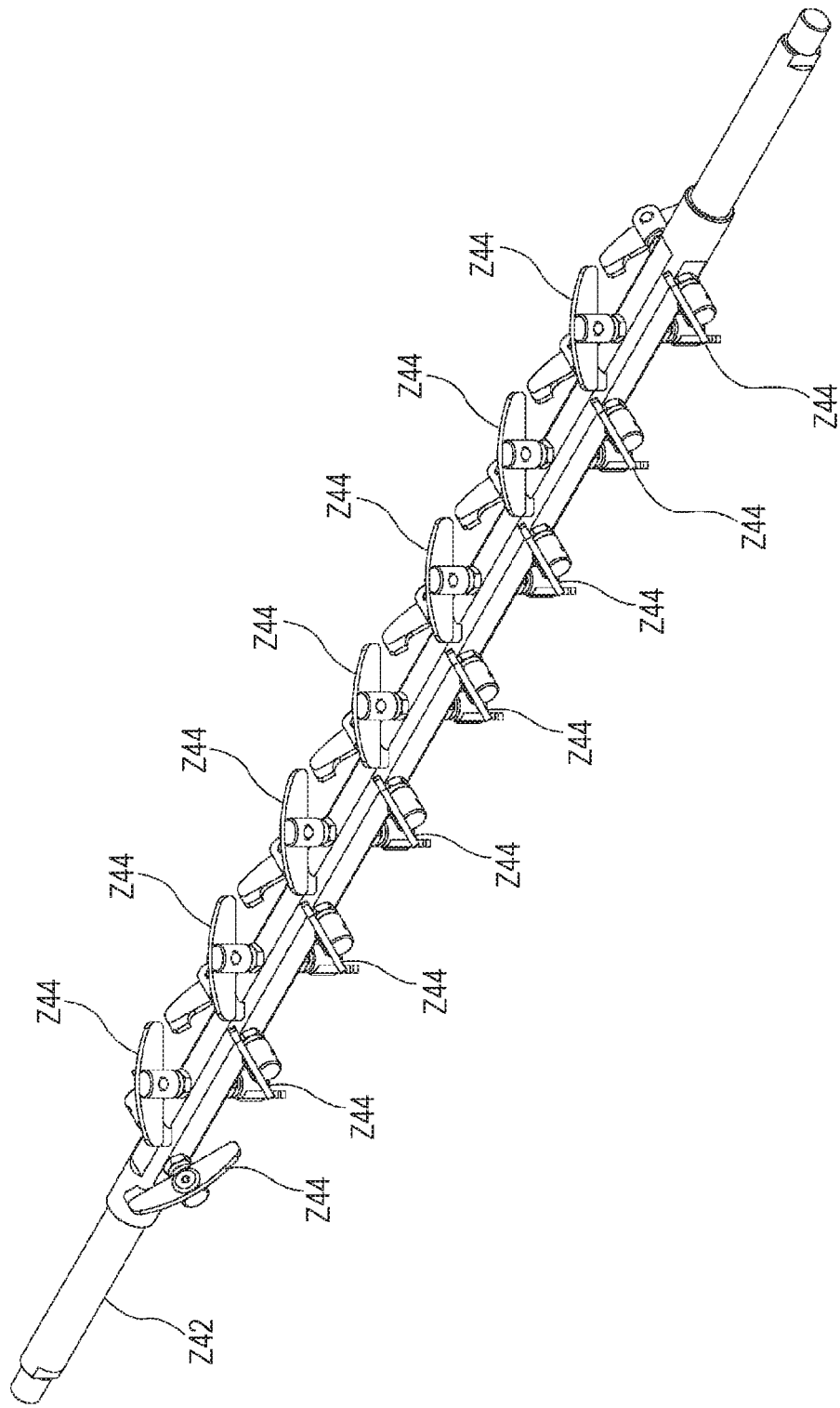
FIG. 9 is a perspective view of an agitation shaft and an agitating rotor (e.g., second mixing member) of a horizontal mixer included in the powdery material mixing and feeding device according to the exemplary embodiment.

The agitation shaft Z42 extends in a longitudinal direction of the case Z41 and is disposed substantially in the center in a sectional view. The agitation shaft Z42 is driven to rotate (i.e., spin) by the motor Z43. As shown exemplary in FIG. 9, the agitating rotor Z44 is attached to the agitation shaft Z42. Rotation of the agitation shaft Z42 causes rotation of the agitating rotor Z44 to simultaneously mix and move the powdery materials toward the discharge port Z413.

The agitating rotor Z44 is configured to agitate and mix the powdery materials fed into the case Z41 through the feed ports (e.g., Z411 and Z412). The agitating rotor Z44 can have any shape, but is preferably configured to simultaneously mix and move the powdery materials toward the discharge port Z413. As shown exemplarily in FIG. 9, the agitating rotor Z44 according to the exemplary embodiment is shaped to have expanded both ends, is attached to the agitation shaft Z42 at a freely adjustable angle.

The third measuring feeder Z1c is configured to measure and feed the horizontal mixer Z4 with a lubricant. The third connecting pipe Z2c is connected to the bottom of the third measuring feeder Z1c. The lubricant in the third measuring feeder Z1c is fed to the horizontal mixer Z4 through the third connecting pipe Z2c (i.e., lubricant feeding). The lubricant can alternatively be fed to the horizontal mixer Z4 by a μR feeder (e.g., manufactured by Nisshin Engineering Inc.). The lubricant can still alternatively be fed to the horizontal mixer Z4 by an atomizer (i.e., a spray device).

The third connecting pipe Z2c includes a branch pipe Z2c1 and a main pipe Z2c2. The branch pipe Z2c1 has a first end connected to the bottom of the third measuring feeder Z1c, and a second end connected to the main pipe Z2c2. The lower end of the main pipe Z2c2 is connected to the second feed port Z412 of the horizontal mixer Z4.

The fourth connecting pipe Z2d has an upper end connected with the discharge port Z413 of the horizontal mixer Z4 and a lower end connected with the feed port Z361 of the buffer tank 19. The mixed powdery materials are fed through the discharge port Z413 of the horizontal mixer Z4 and the fourth connecting pipe Z2d to the buffer tank 19.

The bottom of the buffer tank 19 is connected to the compression-molding machine. The mixed powdery materials passing through the buffer tank 19 are fed to the feeder X in the compression-molding machine and are eventually compression molded in the die bores 4.

The powdery material mixing degree measurement device M thus measures the mixing degree of the mixed powdery materials discharged from the buffer tank 19 of the powdery material mixing and feeding device Z toward the compression-molding machine. If the mixing degree is out of a predetermined range, then the mixed powdery materials are discharged, alarm sound is issued, the device is stopped, or the like. The powdery material mixing degree measurement device M promptly measures the mixing degree of the powdery materials mixed by the powdery material mixing and feeding device Z and operates appropriately.

Examples of a method of measuring a mixing degree of mixed powdery materials include Raman spectroscopy, infrared spectroscopy, X-ray diffraction, X-ray transmission measurement, and high performance liquid chromatography (HPLC). Any one of these methods is applicable to promptly measure a mixing degree of mixed powdery materials. The exemplary embodiment mainly adopts near infrared reflectance (NIR, or a near infrared absorption spectrum method). Specifically, in order to evaluate an amount or a percentage (i.e., ratio) of the principal agent in the mixed powdery materials (i.e., uniformity of the mixed powdery materials) (whether or not the mixed powdery materials are segregated), the mixed powdery materials moving from the powdery material mixing and feeding device Z toward the feeder X of the compression-molding machine are irradiated with near infrared light to measure light absorption and scattering for qualitative and quantitative analyses of a concentration and the like of the principal agent based on a spectrum. These analyses are repeatedly conducted at predetermined cycles. A measured wavelength falls in a wavelength range including a unique absorption peak of the principal agent and no peak of the excipient or the lubricant. The near infrared reflectance also achieves measurement of particle diameters of the mixed powdery materials.

Figure 10:
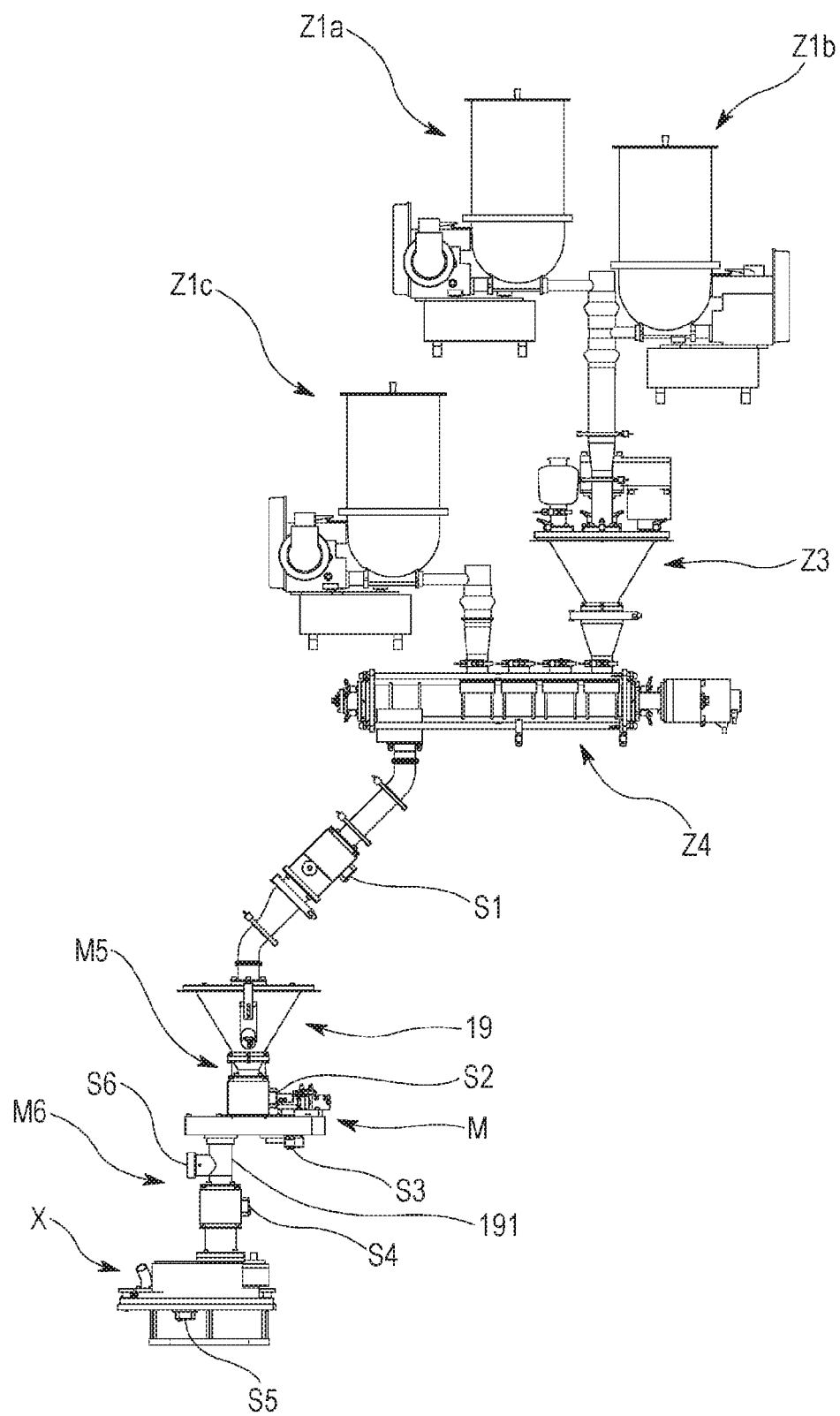
FIG. 10 is a side view of a main part of the powdery material mixing and feeding device according to the exemplary embodiment.
Figure 11:
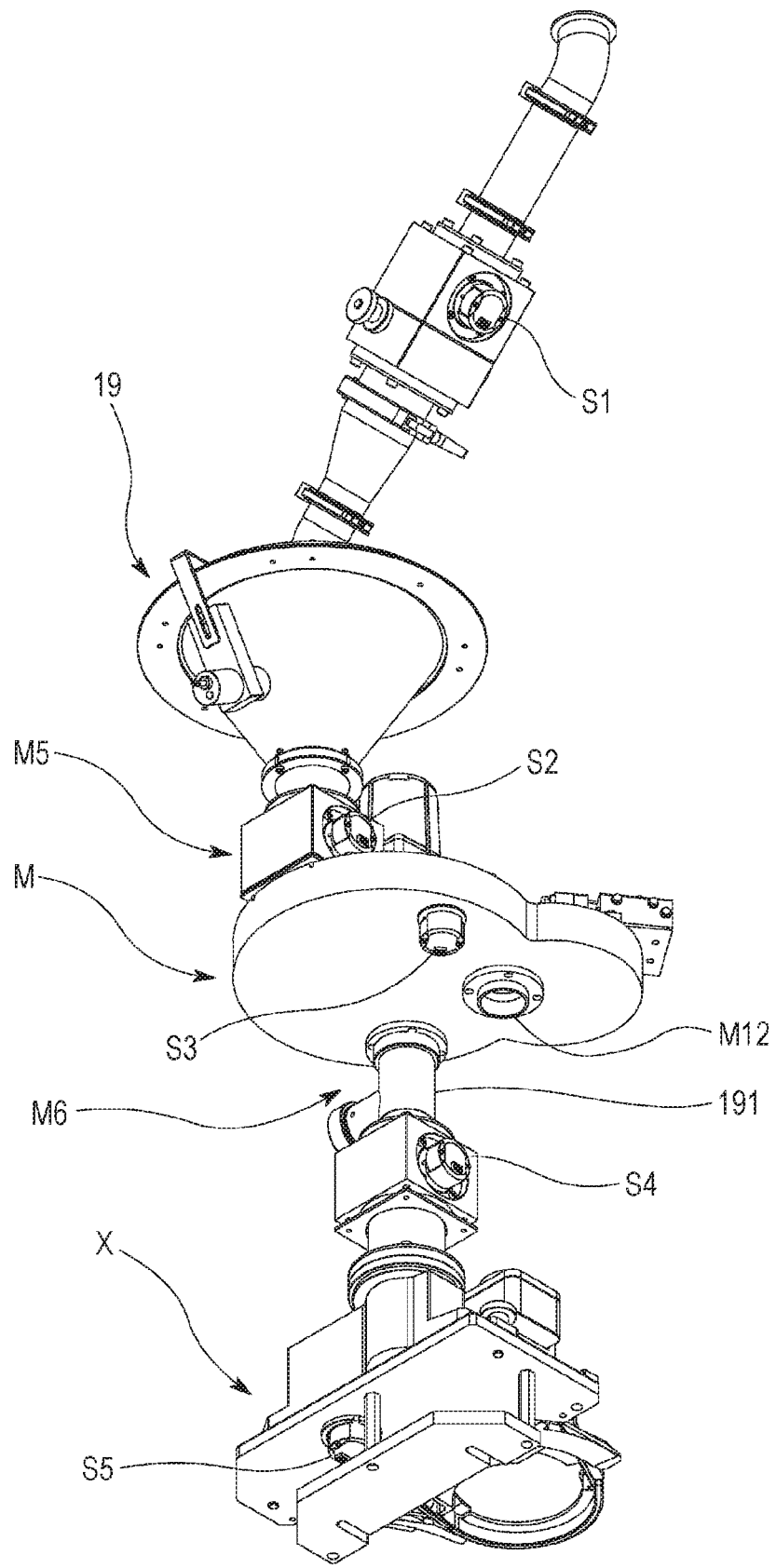
FIG. 11 is a perspective view of the main part of the powdery material mixing and feeding device according to the exemplary embodiment.

The exemplary embodiment adopts a near infrared sensor as a process analytical technology (PAT) sensor configured to measure a mixing degree and the like of powdery materials. As shown exemplarily in FIGS. 10 and 11, the configuration according to the exemplary embodiment includes a first sensor S1 of a near infrared sensor configured to initially measure the mixing degree of the mixed powdery materials before being reserved in the buffer tank 19.

The powdery materials mixed by the powdery material mixing and feeding device Z are temporarily reserved in the buffer tank 19 as a reservoir after the first sensor S1 measures the mixing degree of the powdery materials. The powdery materials reserved in the buffer tank 19 are fed to the powdery material mixing degree measurement device M after a near infrared sensor S2 measures the mixing degree of the powdery materials again. The mixed powdery materials can optionally be further agitated and mixed in the buffer tank 19.

Figure 12:
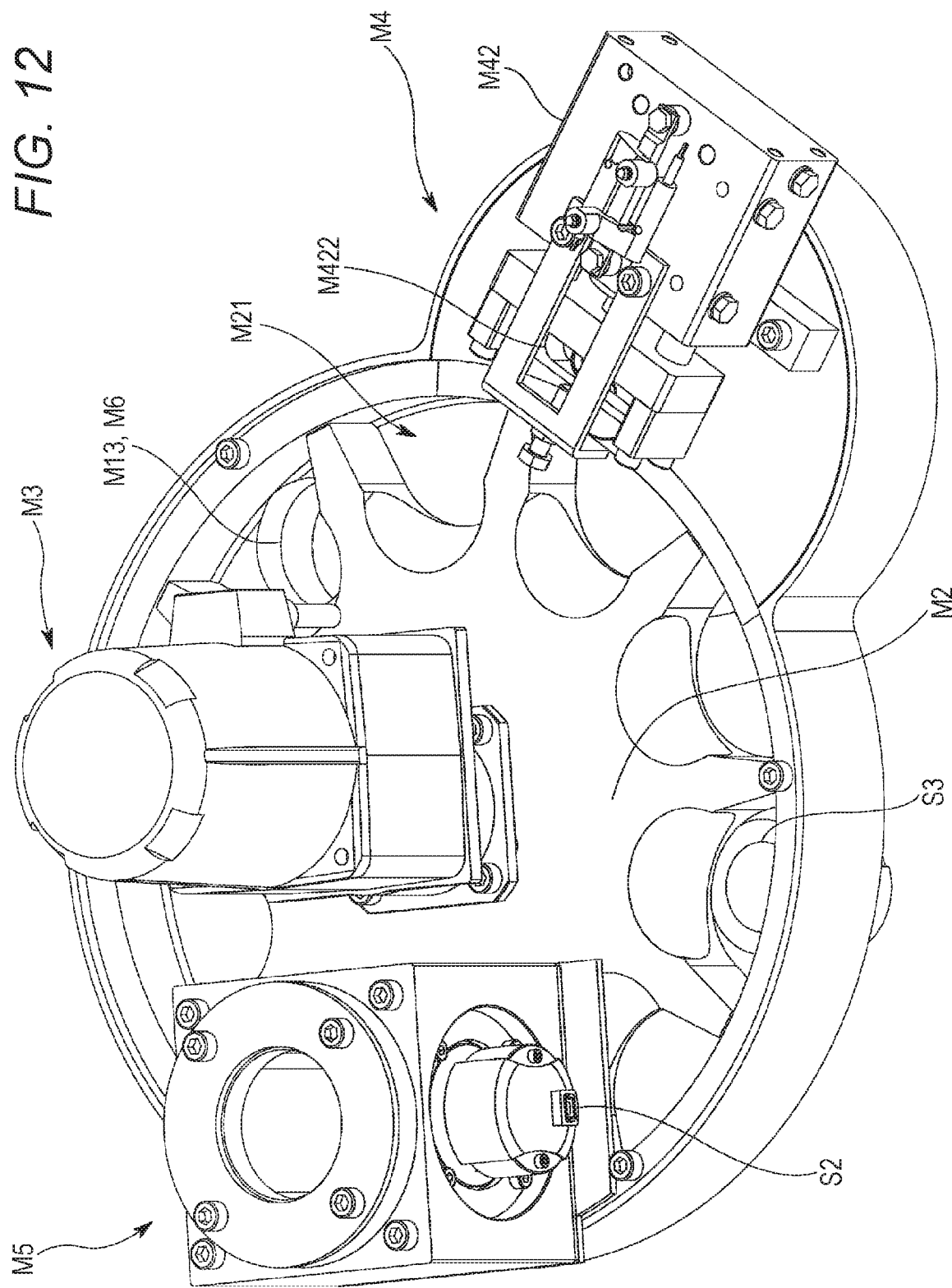
FIG. 12 is a perspective view of a main part of a powdery material mixing degree measurement device according to the exemplary embodiment.
Figure 13:
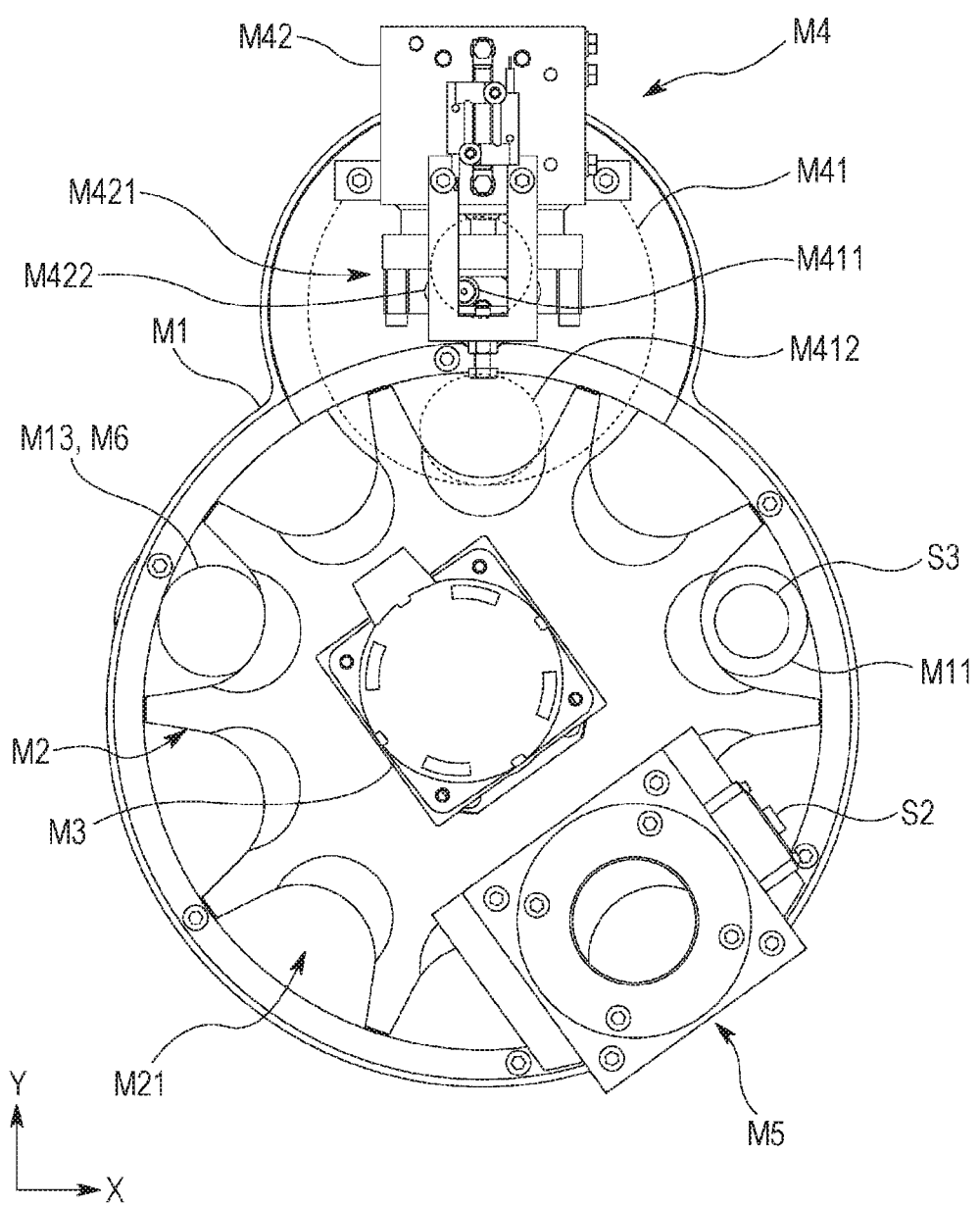
FIG. 13 is a plan view of the main part of the powdery material mixing degree measurement device according to the exemplary embodiment.

As shown exemplarily in FIGS. 12 and 13, the powdery material mixing degree measurement device M includes a case M1, a rotator M2 as a movable member in the case M1, a motor M3 as a driver for the rotator M2, near infrared sensors S2 and S3 configured to measure a mixing degree of powdery materials, a powdery material remover M4 configured to remove defective mixed powdery materials, a feeding unit M5 configured to introduce the mixed powdery materials from the buffer tank 19 into the case M1, and the discharger M6 configured to discharge the mixed powdery materials to the agitated feeder X functioning as a filler of the compression-molding machine.

Figure 14:
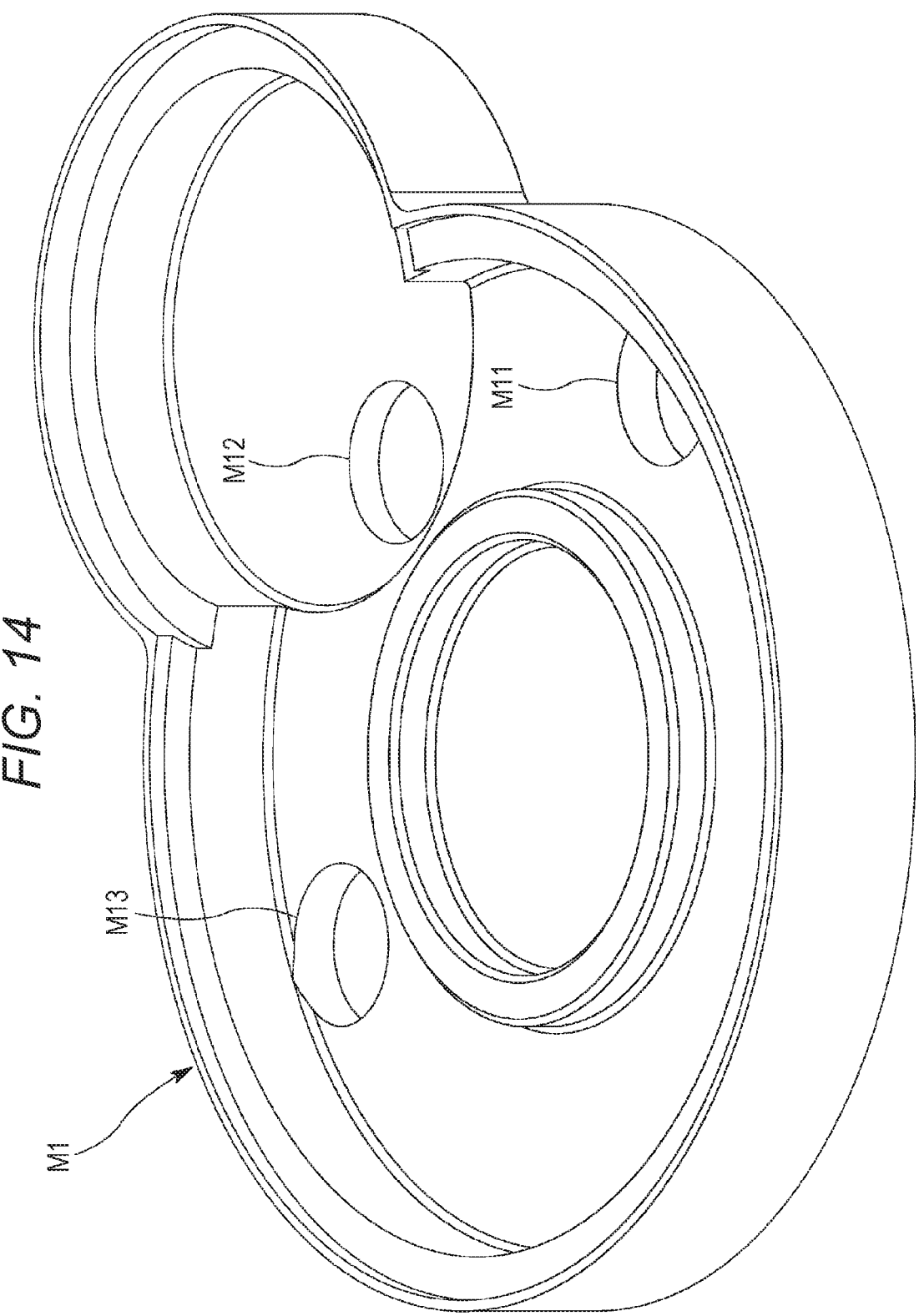
FIG. 14 is a perspective view of a case of the powdery material mixing degree measurement device according to the exemplary embodiment.
Figure 15:
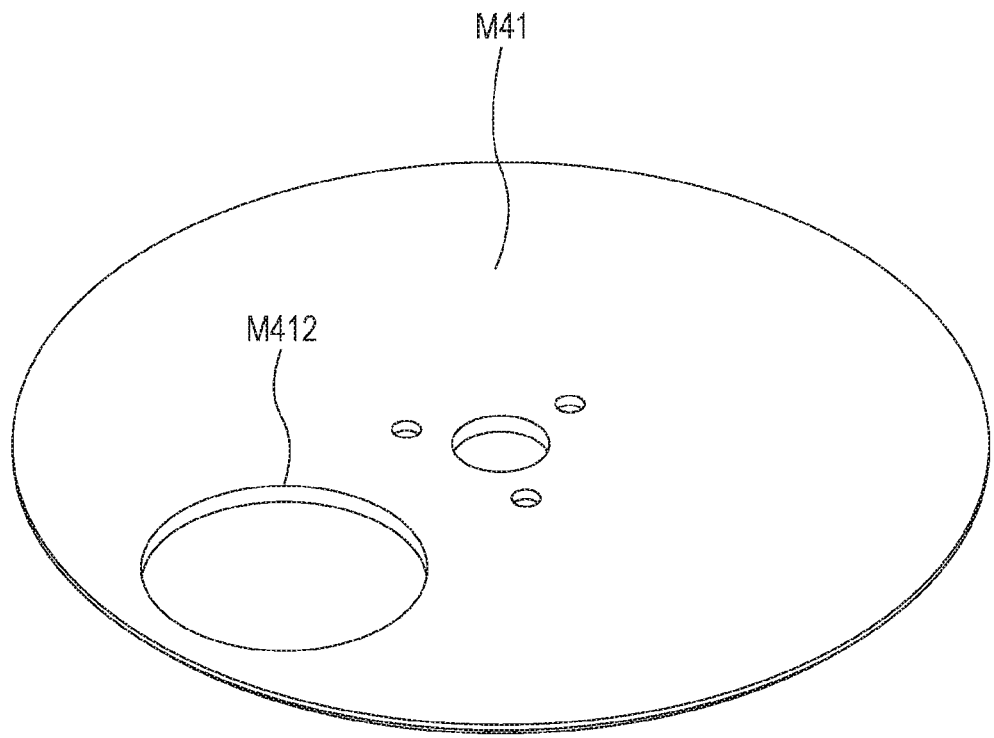
FIG. 15 is a perspective view of a drive body of the powdery material mixing degree measurement device according to the exemplary embodiment.
Figure 16:
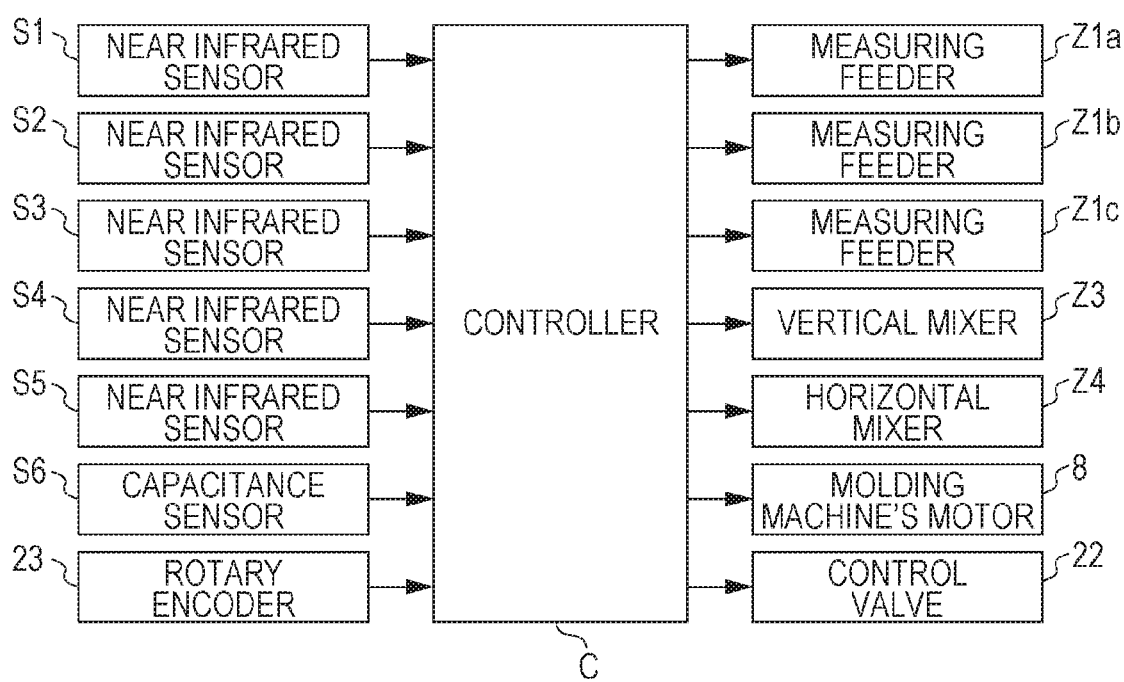
FIG. 16 is a block diagram of a control system in a molded product production system according to the exemplary embodiment.

As shown exemplarily in FIG. 14, the case M1 has a bottom surface including an attachment bore M11 allowing the near infrared sensor S3 to be mounted, a removal bore M12 (the powdery material remover M4) for removal of a powdery material, and a discharge bore M13 (the discharger M6) for discharge of a powdery material to the powdery material feed passage 191. The case M1 has a top surface on which the feeding unit M5 configured to feed the case M1 with a powdery material is mounted. The mixed powdery materials enter the case M1 by way of the buffer tank 19 and the feeding unit M5. The feeding unit M5 has the second sensor S2 of a near infrared sensor configured to measure a mixing degree of mixed powdery materials passing through the feeding unit M5.

The rotator M2 includes a plurality of movable portions M21. The feeding unit M5 feeds the movable portions M21 with the mixed powdery materials. The rotator M2 is driven to rotate by the motor M3 positioned above the rotator M2.

The third sensor S3 of a near infrared sensor is attached to the attachment bore M11 of the case M1 and is configured to measure a mixing degree of powdery materials fed to the movable portions M21.

The powdery material remover M4 includes a case, a drive body M41, and a driver M42 configured to drive the drive body M41. The case of the powdery material remover M4 is provided integrally with the case M1. The drive body M41 according to the exemplary embodiment has a circular disc shape, and includes a center projection M411 engaged with the driver M42, and a partial cutoff portion M412. The driver M42 has a distal end M421 configured to drive forward and backward along a Y axis indicated in FIG. 13, and an engagement bore M422 disposed at the distal end and engaged with the projection M411 of the drive body M41.

In a state where the distal end M421 of the driver M42 moves in a positive direction along the Y axis indicated in FIG. 13, the cutoff portion M412 of the drive body M41 is located in the center of the removal bore M12 of the case M1. In another state where the distal end M421 moves in a negative direction along the Y axis, the cutoff portion M412 is apart from the removal bore M12 of the case M1.

Specifically, in the case where the driver M42 drives to move the distal end M421 in the negative direction along the Y axis, the drive body M41 is driven clockwise together therewith and the cutoff portion M412 is not overlapped with the removal bore M12. A powdery material in the movable portions M21 of the rotator M2 is not removed in this case. In the other case where the driver M42 drives to move the distal end M421 in the positive direction along the Y axis, the drive body M41 is driven counterclockwise together therewith and the cutoff portion M412 is overlapped with the removal bore M12. The powdery material in the movable portions M21 of the rotator M2 is removed in this case.

The drive body M41 according to the exemplary embodiment is driven clockwise and counterclockwise to remove the powdery material in the movable portions M21 of the rotator M2. The drive body M41 can alternatively be configured to rotate only in one direction to remove the powdery material in the movable portions M21.

If the mixing degree of the powdery materials measured with any of the first to third sensors S1 to S3 (i.e., the amount or the percentage (i.e., ratio) of the principal agent in the mixed powdery materials), is out of the predetermined range, then the powdery material remover M4 removes the mixed powdery materials in the movable portions M21. The mixed powdery materials in the movable portions M21 can alternatively be removed if all mixing degree measurement values of the first to third sensors S1 to S3 are out of the predetermined range, or if the measurement value of any one of the sensors S is out of the predetermined range.

The powdery material remover M4 is also configured to sample the mixed powdery materials.

The mixed powdery materials not removed by the powdery material remover M4 pass through the discharge bore M13 to reach the powdery material feed passage 191. The mixed powdery materials move to the discharger M6 in this case.

A fourth sensor S4 of a near infrared sensor measures the mixing degree of the mixed powdery materials reached the powdery material feed passage 191 before the mixed powdery materials are guided into the agitated feeder X functioning as a filler of the compression-molding machine. Furthermore, a fifth sensor S5 of a near infrared sensor measures the mixing degree of the mixed powdery materials in the agitated feeder X of the compression-molding machine according to the exemplary embodiment.

If the mixing degree of the mixed powdery materials measured by the fourth sensor S4 and/or the fifth sensor S5 is out of the predetermined range, then the mixed powdery materials in the feeder X are filled in each of the die bores 4 of the table 31 of the compression-molding machine and are compression molded by the upper and lower punches 5 and 6 into the shape of a molded product. The molded product is then removed by the molded product removal mechanism W before reaching the molded product collecting position 18. Specifically, in the compression-molding machine, the control valve 22 is opened when the die bore 4 filled with defective mixed powdery materials tableted into a molded product passes by the air spray nozzle 16a, and the air spray nozzle 16a sprays air to blow the molded product out of the table 31.

In summary, the powdery material remover M4 removes the mixed powdery materials if any of the first to third sensors 51 to S3 detects a mixing degree of the mixed powdery materials out of the predetermined range, and the molded product removal mechanism W removes the compression molded mixed powdery materials if the fourth sensor S4 and/or the fifth sensor S5 detects a mixing degree of the mixed powdery materials out of the predetermined range.

Summarized again below is continuous production of compression-molded products by a system including the compression-molding machine, the powdery material mixing and feeding device Z, and the powdery material mixing degree measurement device M according to the exemplary embodiment. Initially, the first measuring feeder Z1a simultaneously measures and feeds the principal agent, and the second measuring feeder Z1b simultaneously measures and feeds the excipient or the like (i.e., measuring and feeding). The vertical mixer Z3 functioning as the first mixer is subsequently fed with the powdery materials of the principal agent and the excipient or the like and mixes the powdery materials therein (i.e., first mixing). In the vertical mixer Z3, the agitating rotor Z34 rotates about the agitation shaft Z33 disposed substantially vertically, to mix the powdery materials of the principal agent and the excipient or the like.

The horizontal mixer Z4 functioning as the second mixer is fed with the mixed powdery materials of the principal agent and the excipient or the like subjected to the first mixing and mixes the powdery materials again (i.e., second mixing). In the horizontal mixer Z4, the agitating rotor Z44 rotates about the agitation shaft Z42 disposed substantially horizontally, to mix the powdery materials of the principal agent and the excipient or the like. Such a process may achieve improvement in mixing degree of the at least two types of powdery materials (e.g., the principal agent and the excipient or the like), and may cause less segregation of the principal agent. Third mixing of feeding another vertical mixer with the powdery materials and mixing the powdery materials therein can optionally be conducted after the second mixing by the horizontal mixer Z4. This will achieve further improvement in a mixing degree of the powdery materials.

The first mixing preferably includes reserving at least a part of the powdery materials. Specifically, the powdery materials pass through the plurality of bores Z321 of the powdery material passing member Z32. The reservoir Z30 reserves powdery materials by an increase in an amount of the powdery materials to be fed to the first vertical mixer Z3a to be more than the powdery materials passing through the bores Z321 or increase in rotational speed of the auxiliary rotor Z35. The powdery materials then pass through the bores Z321 while being agitated and mixed by the auxiliary rotor Z35.

Furthermore, the third measuring feeder Z1c simultaneously measures and feeds the lubricant (i.e., lubricant feeding). The lubricant is fed to the horizontal mixer Z4 in the exemplary embodiment, but can alternatively be fed to a second vertical mixer Z3b, the feeder X, or the like, with no limitation in feeding destination of the lubricant. The lubricant can be fed by the µR feeder (e g, manufactured by Nisshin Engineering Inc.) or by an atomizer (i.e., spray device).

The mixed powdery materials including the principal agent, the excipient or the like, and the lubricant are fed to the buffer tank 19 of the compression-molding machine. The sensors S2 and S3 then measure the mixing degree of the mixed powdery materials fed to the buffer tank 19 (i.e., measuring). Obviously, the sensor S1 can measure the mixing degree of the mixed powdery materials before the mixed powdery materials are fed to the buffer tank 19.

The mixed powdery materials are removed if the measured mixing degree of the mixed powdery materials is out of the predetermined range (i.e., removing). The mixed powdery materials are subsequently fed to the feeder X functioning as a filler. The sensor S5 can measure the mixing degree of the mixed powdery materials in the feeder X, or the sensor S4 can measure the mixing degree of the mixed powdery materials immediately before the mixed powdery materials are fed to the feeder X.

The mixed powdery materials fed to the feeder X are filled in the die bores 4 of the table 31 of the turret 3 in the compression-molding machine (i.e., filling). The mixed powdery materials filled in each of the die bores 4 are compression molded by the upper and lower punches 5 and 6 (i.e., compression molding). The mixed powdery materials thus compression molded into a molded product are guided by the guide member 17 and are collected at the molded product collecting position 18. The controller C in the system according to the exemplary embodiment causes the fourth sensor S4 and/or the fifth sensor S5 to repeatedly measure the mixing degree of the mixed powdery materials fed by the powdery material mixing and feeding device Z to the feeder X and filled in the die bores 4. If the measured mixing degree of the mixed powdery materials is out of the predetermined range, the molded product removal mechanism W in the compression-molding machine removes a defective molded product compression molded in the die bore 4 filled with the mixed powdery materials (i.e., molded product removing). When the die bore 4 assumed to be filled with such defective mixed powdery materials having a mixing degree out of the predetermined range (i.e. the possibly defective molded product) passes by the air spray nozzle 16*a* is found by referring to an output signal from the rotary encoder 23.

Prior to the filling the die bores 4 with the powdery materials in the compression-molding machine, the lubricant (i.e., external lubricant) can optionally be sprayed to the lower end surface of the upper punch 5, the upper end surface of the lower punch 6, and the inner circumferential surface of the die bore 4 (i.e., lubricant feeding).

The first measuring feeder Z1*a* is configured to feedback control weight (i.e., a flow rate) of the fed principal agent per unit time, the second measuring feeder Z1*b* is configured to feedback control weight of the fed excipient or the like per unit time, and the third measuring feeder Z1*c* is configured to feedback control weight of the fed lubricant per unit time. Furthermore, these powdery materials are to be mixed at a desired mixture ratio. Even in this configuration, the amounts of the powdery materials discharged from the measuring feeders Z1 and fed to the mixers Z3 and Z4 can somehow deviate from initial target amounts. The powdery material fed from any of the measuring feeders Z1 to the mixers Z3 and Z4 is sometimes smaller in amount than the target amount. In such a case, the amount of the principal agent in the mixed powdery materials has a ratio larger or smaller than the desired ratio. A molded product obtained by compression molding such mixed powdery materials is defective and will fail to exert an expected drug effect.

Even if the mixers Z3 and Z4 fail to adequately mix the powdery materials and the mixed powdery materials fed to the feeder X of the compression-molding machine has segregation of the principal agent or the excipient, molded products will be defective with different contents.

The controller C in the system according to the exemplary embodiment adjusts, in accordance with the mixing degree measurement value of the mixed powdery materials by any of the first to fifth sensors S1 to S5, the amounts of the powdery materials fed by the measuring feeders Z1*a* to Z1*c*, rotational speed of each of the agitation shaft Z33, the agitating rotor Z34, and the auxiliary rotor Z35 of the vertical mixer Z3, rotational speed of each of the agitation shaft Z42 and the agitating rotor Z44 of the horizontal mixer Z4, and rotational speed of the turret 3 of the compression-molding machine. Examples of the controller C include a microcomputer system including a processor, a memory, an auxiliary storage device, and an input/output interface, a programmable controller, a general-purpose personal computer, and a work station.

In a case where the absolute value of a difference between a target value and the amount or the percentage of the principal agent in the mixed powdery materials repeatedly measured by any of the first to fifth sensors S1 to S5 is more than a predetermined threshold (i.e., the percentage of the principal agent is inappropriately small or large) continuously for at least a certain period, at least one of the first to third measuring feeders Z1*a* to Z1*c* is regarded as failing to feed an appropriate amount of the powdery materials. In this case, the controller C temporarily interrupts weight feedback control by the measuring feeders Z1 itself and adjusts a rotational speed of a drive motor of each of the measuring feeders Z1 such that the amount or the percentage of the principal agent in the mixed powdery materials measured by any of the first to fifth sensors S1 to S5 is approximate to the target value. In a case where the amount or the percentage of the principal agent in the mixed powdery materials is less than the target value, the first measuring feeder Z1*a* increases the amount of the discharged principal agent, and/or the second and third measuring feeders Z1*b* and Z1*c* decrease the amounts of the discharged excipient or the like and the discharged lubricant, respectively. In another case where the amount or the percentage of the principal agent in the mixed powdery materials is more than the target value, the first measuring feeder Z1*a* decreases the amount of the discharged principal agent, and/or the second and third measuring feeders Z1*b* and Z1*c* increase the amounts of the discharged excipient or the like and the discharged lubricant, respectively.

Alternatively, if the absolute value of the difference between the target value and the amount or the percentage of the principal agent in the mixed powdery materials is more than the threshold continuously for at least a certain period, the target value of the discharged amount of the powdery materials commanded by the controller C to the measuring feeders Z1*a* to Z1*c* can be changed to optimize the amount of the fed principal agent. In a case where the amount or the percentage of the principal agent in the mixed powdery materials is less than the target value, the first measuring feeder Z1*a* has a higher target value of the amount of the discharged principal agent, and/or the second and third measuring feeders Z1*b* and Z1*c* have lower target values of the amounts of the discharged excipient or the like and the discharged lubricant, respectively. In another case where the amount or the percentage of the principal agent in the mixed powdery materials is more than the target value, the first measuring feeder Z1*a* has a lower target value of the amount of the discharged principal agent, and/or the second and third measuring feeders Z1*b* and Z1*c* have higher target values of the amounts of the discharged excipient or the like and the discharged lubricant, respectively.

In a case where the absolute value of the difference between the target value and the amount or the percentage of the principal agent in the mixed powdery materials repeatedly measured by any of the first to fifth sensors S1 to S5 is not more than the threshold continuously for at least a certain period but is more than the threshold instantaneously or only for a short period, (the principal agent, the excipient or the like, or the lubricant of) the mixed powdery materials moving toward the feeder X of the compression-molding machine is regarded as having segregation, i.e. locally having portions of high and low concentrations of the principal agent. In this case, the controller C changes (i.e., increases or decreases) current rotational speed of each of the agitation shaft Z33 and the agitating rotors Z34 and Z35 of the vertical mixer Z3, and/or changes (i.e., increases or decreases) current rotational speed of each of the agitation shaft Z42 and the agitating rotor Z44 of the horizontal mixer Z4, for further improvement in mixing degree of the powdery materials.

As described above, increasing or decreasing each of the amounts of the powdery materials discharged from the measuring feeders Z1*a* to Z1*c*, changing a rotational speed of the agitation shaft Z33 of the vertical mixer Z3, or changing a rotational speed of the agitation shaft Z42 of the horizontal mixer Z4 can possibly change the flow rate per unit time of the mixed powdery materials fed to the feeder X through the powdery material feed passage 191. If the turret 3 and the upper and lower punches 5 and 6 are kept rotating at constant rotational speed despite the fact that the flow rate of the mixed powdery materials fed to the feeder X is changed, the compression-molding machine has the unchanged amount of the used mixed powdery materials per unit time. In this case, the powdery materials to be filled in the die bores 4 will be short or the used amount is less than the fed amount to overflow powdery materials from the feeder X or the die bores 4. Either one of these cases will cause failure in production of molded products.

The controller C in the system according to the exemplary embodiment thus causes a flowmeter S6 to measure the flow rate of the mixed powdery materials fed to the feeder X through the powdery material feed passage 191 and adjusts rotational speed of the turret 3 and the punches 5 and 6 of the compression-molding machine in accordance with a level of the flow rate. Specifically, the controller C controls the motor 8 to increase the rotational speed of the turret 3 and the punches 5 and 6 as the flow rate of the mixed powdery materials fed to the feeder X increases, and to decrease the rotational speed of the turret 3 and the punches 5 and 6 as the flow rate of the mixed powdery materials fed to the feeder X decreases. The flowmeter S6 is configured by a capacitance sensor or the like.

The exemplary embodiment provides a molded product production system including a powdery material mixing and feeding device Z configured to feed mixed powdery materials including at least two types of powdery materials, a filler X configured to fill, with the mixed powdery materials fed by the powdery material mixing and feeding device Z, a die bore 4 of a compression-molding machine configured to compress a powdery material to mold a molded product, a sensor S4 or S5 configured to measure a mixing degree of the mixed powdery materials fed by the powdery material mixing and feeding device Z to the filler X via a powdery material mixing degree measurement device M and filled in the die bore 4, and a molded product removal mechanism W configured to distinguish a molded product obtained by compression molding mixed powdery materials having a mixing degree measured by the sensor S4 or S5 out of a predetermined range from a molded product obtained by compression molding mixed powdery materials having a mixing degree within the predetermined range. The exemplary embodiment achieves appropriately monitoring the mixing degree of the mixed powdery materials and maintaining quality of the molded product obtained by compression molding the mixed powdery materials.

The invention is not limited to the exemplary embodiment detailed above. For example, the number of the sensors configured to measure a mixing degree of mixed powdery materials is set appropriately, with no limitation to five.

A powdery material can be fed by a device having a feeding function similar to that of the μR feeder (e.g., manufactured by Nisshin Engineering Inc.). The powdery materials in the mixer can be mixed while stopping feed of powdery materials to the mixer (i.e., the first mixer or the second mixer).

The molded product removal mechanism W, which is configured to distinguish a molded product obtained by compression molding mixed powdery materials having a mixing degree measured by the sensor S4 or S5 out of the predetermined range from a molded product obtained by compression molding mixed powdery materials having a mixing degree within the predetermined range, is not limited in terms of its specific aspect to a mechanism configured to spray high-pressure air from the nozzle 16a to a target molded product as in the above exemplary embodiment. Adoptable examples of the molded product removal mechanism include various known mechanisms configured to specify and select a certain molded product from among remaining molded products. The molded product removal mechanism can alternatively be disposed outside the compression-molding machine.

Moreover, specific configurations of the respective portions can be modified without departing from the spirit of the invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Further, Applicant's intent is to encompass the equivalents of all claim elements, and no amendment to any claim of the present application should be construed as a disclaimer of any interest in or right to an equivalent of any element or feature of the amended claim.

What is claimed is:

1. A molded product production system, comprising:
a powdery material mixing and feeding device configured to feed mixed powdery materials including at least two types of powdery materials;
a filler configured to fill, with the mixed powdery materials fed by the powdery material mixing and feeding device, a die bore of a compression-molding machine configured to compress a powdery material to mold a molded product;
a powdery material feed passage comprising a discharger located between the powdery material mixing and feeding device and the filler, the discharger discharging the mixed powdery materials to the filler;
a first sensor configured to measure, prior to filling the discharger, a mixing degree of the mixed powdery materials fed to the discharger by the powdery material mixing and feeding device;
a second sensor configured to measure, prior to filling the die bore, the mixing degree of the mixed powdery materials fed by the discharger to the filler;
a molded product removal mechanism configured to, based on a result of a measurement of the second sensor performed prior to filling the die bore, distinguish and remove a molded product obtained by compression molding mixed powdery materials having a mixing degree measured by the second sensor out of a predetermined range from a molded product obtained by compression molding mixed powdery materials having a mixing degree within the predetermined range; and
a powdery material remover configured to, based on a result of a measurement of the first sensor performed prior to filling the discharger, distinguish and remove the mixed powdery materials, having the mixing degree measured by the first sensor out of the predetermined range, prior to filling the die bore.

2. The molded product production system according to claim 1, wherein the first sensor is disposed at the filler, and the second sensor is disposed between the powdery material mixing and feeding device and the filler.

3. The molded product production system according to claim 1, wherein the molded product removal mechanism is configured to sample the molded product.

4. The molded product production system according to claim 2, wherein the molded product removal mechanism is configured to sample the molded product.

5. The molded product production system according to claim 1, wherein the second sensor is disposed at the filler at a location prior to an entrance of the die bore.

6. The molded product production system according to claim 1, wherein the first sensor is disposed, between the powdery material mixing and feeding device and the filler, at a location prior to an entrance of the die bore.

7. The molded product production system according to claim 1, wherein the first sensor and the second sensor measure the mixing degree of the mixed powdery materials only at locations prior to an entrance of the die bore.

8. The molded product production system according to claim 1, wherein the molded product removal mechanism comprises:
   a guide member that guides the molded product pushed out of the die bore, and
   wherein the guide member includes a proximal end located at a molded-product collecting position and a distal end located closer to a center of a table of a turret of the compression-molding machine than a rotation locus of the die bore.

9. The molded product production system according to claim 8, wherein the guide member is provided with an air passage for a pressurized air flow, and the air passage includes an end as an air spray nozzle opened in a radial direction of the turret.

10. The molded product production system according to claim 9, wherein the molded product removal mechanism further comprises:
    a control valve disposed on a flow passage to open and close the flow passage, and
    wherein, when the molded product is out of the predetermined range, the control valve opens to pushed the molded product, which is out of the predetermined range, out of the die bore.

11. The molded product production system according to claim 10, wherein the molded product, which is out of the predetermined range, is pushed out of the die bore by air provided by the air spray nozzle before contacting the guide member.

12. The molded product production system according to claim 11, wherein the molded product removal mechanism is configured such that the molded product that is out of the predetermined range and is pushed out of the die bore fails to reach the molded-product collecting position ahead of the guide member.

13. The molded product production system according to claim 1, wherein the first sensor includes a plurality of sensors,
    wherein a first one of the plurality of sensors measures the mixing degree of the mixed powdery materials between the discharger and the powdery material mixing and feeding device,
    wherein a second one of the plurality of sensors measures the mixing degree of the mixed powdery materials at the discharger, and
    wherein a third one of the plurality of sensors measures the mixing degree of the mixed powdery materials between the discharger and the filler.

14. A method of producing a compression-molded product with a, compression-molding machine from mixed powdery materials including at least two types of powdery materials, the method comprising:
    mixing the at least two types of powdery materials;
    discharging by a discharger, the mixed powdery materials to a filler;
    a first measuring, prior to filling the discharger, of a mixing degree of the mixed powdery materials with a first sensor;
    a second measuring of the mixing degree of the mixed powdery materials fed by the discharger to the filler with a second sensor;
    after the second measuring, filling a die bore of the compression-molding machine with the mixed powdery materials by the filler;
    compression molding, after the filling, the mixed powdery materials filled in the die bore, with an upper punch and a lower punch of the compression-molding machine;
    based on a result of the second measuring by the second sensor prior to the filling of the die bore, removing a molded product by distinguishing, in the compression-molding machine, a molded product obtained by compression molding mixed powdery materials having a mixing degree measured by the second sensor out of a predetermined range from a molded product obtained by compression molding mixed powdery materials having a mixing degree within the predetermined range, and
    based on a result, of the first measuring by the first sensor performed prior to filling the discharger, distinguishing and removing the mixed powdery materials, having the mixing degree measured by the first sensor out of the predetermined range, prior to filling the die bore.

15. The method of producing the compression-molded product according to claim 14, wherein the second measuring of the mixing degree of the mixed powdery materials includes placing the second sensor at the filler that fills the die bore with the mixed powdery materials.

16. The method of producing the compression-molded product according to claim 14, wherein the first measuring of the mixing degree of the mixed powdery materials includes placing the first sensor between the filler that fills the die bore with the mixed powdery materials and a powdery material mixing and feeding device that feeds the mixed powdery materials to the discharger.

17. The method of producing the compression-molded product according to claim 14, wherein the distinguishing comprises sampling a molded product of the compression molding.

18. The method of producing the compression-molded product according to claim 14, wherein the first sensor and the second sensor measure the mixing degree of the mixed powdery materials only at locations prior to an entrance of the die bore.

19. The method of producing the compression-molded product according to claim 14, wherein the compression-molding machine comprises:
    a guide member that guides the molded product pushed out of the die bore, and
    wherein the guide member includes a proximal end located at a molded-product collecting position and a distal end located closer to a center of a table of a turret of the compression-molding machine than a rotation locus of the die bore.

20. The method of producing the compression-molded product according to claim 19, wherein the guide member is provided with an air passage for a pressurized air flow, and the air passage includes an end as an air spray nozzle opened in a radial direction of the turret,
    wherein the compression-molding machine further comprises a control valve disposed on a flow passage to open and close the flow passage, and wherein when the molded product is out of the predetermined range, the control valve opens to pushed the molded product, which is out of the Predetermined range, out of the die bore.

\* \* \* \* \*